US006207393B1

(12) United States Patent
Shaw et al.

(10) Patent No.: US 6,207,393 B1
(45) Date of Patent: Mar. 27, 2001

(54) INHIBITION OF INTRACELLULAR SIGNAL TRANSDUCTION BY 14-3-3-BINDING PEPTIDES

(75) Inventors: Andrey S. Shaw; Anthony J. Muslin, both of St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 09/326,440

(22) Filed: Jun. 4, 1999

Related U.S. Application Data

(62) Division of application No. 08/616,669, filed on Mar. 15, 1996, now Pat. No. 5,948,765.

(51) Int. Cl.[7] .............................. G01N 33/53; C12N 9/12; A61K 38/00
(52) U.S. Cl. ............................. 435/7.1; 435/194; 514/2; 514/12
(58) Field of Search ..................... 435/7.1, 196; 514/2, 514/12

(56) References Cited

U.S. PATENT DOCUMENTS 5,597,719   1/1997   Freed et al. ..................... 435/194

OTHER PUBLICATIONS

Morrison et al. J. Biol. Chem., 268, 17309–17316, Aug. 1993.*
Moorhead et al. Current Biology, 6, 1104–1113, Sep. 1996.*
Aitken et al., 14–3–3 Proteins: A Highly Conserved, Widespread Family of Eukaryotic Proteins, *Trends Biochem. Sci.* 17:498–501 (1992).
Aitken, 14–3–3 Proteins on the MAP, *Trends Biochem. Sci.* 20:95–97 (1995).
Carroll et al., Protein Kinase C–mediated Serine Phosphorylation Directly Activates Raf–1 in Murine Hematopoietic Cells, *J. Bio. Chem.* 269:1249–1256 (1994).
Daum et al., The Ins and Outs of Raf Kinases, *Trends Biochem. Sci.* 19:474–480 (1994).
Dent et al., Reversal of Raf–1 Activation by Purified and Membrane–Associated Protein Phosphatases, *Science* 268:1902–1906 (1995).
Fabian et al., Requirement for Raf and MAP Kinase Function During the Meiotic Maturation of Xenopus Oocytes, *J. Cell Biol.* 122:645–652 (1993).
Fantl et al., Activation of Raf–1 by 14–3–3 Proteins, *Nature* 371:612–614 (1994).
Freed et al., Binding of 14–3–3 Proteins to the Protein Kinase Raf and Effects on its Activation, *Science* 265:1713–1716 (1994).
Guan et al., Eukaryotic Proteins Expressed in *Escherichia coli* An Improved Thrombin Cleavage and Purification Procedure of Fusion Proteins with Glutathione S–Transferase, *Anal. Bicohem.* 192:262–267 (1991).
Ichimura et al., Molecular Cloning of cDNA Coding for Brain–Specific 14–3–3 Protewin, a Protein Kinase–Dependent Activator of Tyrosine and Tryptophan Hydroxylases, *Proc. Natl. Acad. Sci. USA* 85:7084–7088 (1988).
Irie et al., Stimulatory Effects of Yeast and Mammalian 14–3–3 Proteins of the Raf Protein Kinase, *Science* 265:1716–1719 (1994).
Jonsson et al., Real–Time Biospecific Interaction Analysis Using Surface Plasmon Resonance and a Sensor Chip Technology, *Biotech.* 11:620–627 (1991).

(List continued on next page.)

*Primary Examiner*—Michael Borin
(74) *Attorney, Agent, or Firm*—Howell & Haferkamp, LC

(57) ABSTRACT

Compositions and methods for inhibition of the intracellular activation of a signal transducing protein comprising phosphoserine containing peptides derived from the Raf-1 protein are disclosed. The peptides bind to 14-3-3 protein and thereby prevent its association with the signal transducing peptide to block signal transduction. Also provided is an assay method for identifying a pharmacologic agent that can bind 14-3-3 protein and block signal transduction.

27 Claims, 8 Drawing Sheets

OTHER PUBLICATIONS

Kolch et al., Protein Kinase Cα Activates RAF–1 by Direct Phosphorylation, *Nature* 364:249–252 (1993).

Li et al., Regulation of Raf–1 Kinase Activity by the 14–3–3 Family of Proteins, *EMBO J.* 14:685–696 (1995).

Michaud et al., 14–3–3 is not Essential for Raf–1 Function: Identification of Raf–1 Proteins that are Biologically Activated in a 14–3–3– and Ras–Independent Manner, *Mol. Cell Biol.* 15:3390–3397 (1995).

Moorhead et al., Phosphorylated nitrate reductase from spinach leaves in inhibited in 14–3–3 proteins and activated by fusicoccin, *Current Biology* 6(9):1104–1113 (1996).

Morrison et al., Identification of the Major Phosphorylation Sites of the Raf–1 Kinase, *J. Biol. Chem.* 268:17309–17316 (1993).

Muslin et al., Raf–1 Protein Kinase Is Important for Progesterone–Induced Xenopus Oocyte Maturation and Acts Downstream of mos, *Mol. Cell Biol.* 13:4197–4202 (1993).

Panayotou et al., Interactions Between SH2 Domains and Tyrosine–Phosphorylated Platelet–Derived Growth Factor β–Receptor Sequences: Analysis of Kinetic Parameters by a Novel Biosensor–Based Approach, *Mol. Cell Biol.* 13:3567–3576 (1993).

Payne et al., Kinetics of $p56^{lck}$ and $p60^{src}$ Src Homology 2 Domain Binding to Tyrosine–Phosphorylated Peptides Determined by a Competition Assay or Surface Plasmon Resonance, *Proc. Natl. Acad. Sci. USA* 90:4902–4906 (1993).

Prendergast et al., Ras Regulatory Interactions: Novel Targets for Anti–Cancer Intervention? *BioEssays* 16:187–191 (1994).

Tanji et al., Activation of Protein Kinase C by Purified Bovine Brain 14–3–3: Comparison with Tyrosine Hydroxylase Activiation, *J. Nueurochem.* 63:1908–1916 (1994).

Toker et al., Protein Kinase C Inhibitor Proteins, *Eur. J. Biochem.* 191:421–429 (1990).

\* cited by examiner

A

B

INHIBITION OF INTRACELLULAR SIGNAL TRANSDUCTION BY 14-3-3-BINDING PEPTIDES

This is a divisional of application Ser. No. 08/616,669; filed on Mar. 15, 1996, now U.S. Pat. No. 5,948,765.

BACKGROUND OF THE INVENTION (1) Field of the Invention

This invention relates to intracellular proteins involved in signal transduction and, more particularly, to peptides and methods for blocking signal transduction by binding to 14-3-3 proteins.

(2) Description of the Related Art

The family of proteins known as 14-3-3 proteins are expressed in a wide variety of organisms and tissues and at least seven different isoforms exist in mammalian cells (Aitken et al., *Trends Biochem Sci* 17:498–501, 1992; Aitken, *Trends Biochem Sci* 20:95–97, 1995 which are incorporated by reference). The 14-3-3 proteins appear to mediate a number of biological activities. This protein has been found to activate neuronal tyrosine and tryptophan hydroxylase (Ichimura et al., *Proc Natl Acad Sci USA* 85: 7084–8, 1988 which is incorporated by reference); to regulate the activity of protein kinase C (Isobe et al. *FEBS Letters* 308:121–124, 1991; Toker et al. *Eur J Biochem* 191: 421–9, 1990; Tanji et al., *J. Neurochem* 63: 1908–16, 1994 which are incorporated by reference); as well as to bind to and presumably regulate a number of signaling proteins including Raf-1, polyoma middle T antigen, bcr, and PI-3 kinase (Fantl et al., *Nature* 371: 612–4, 1994 which is incorporated by reference).

One of these proteins, Raf, constitutes a family of serine/threonine kinases involved in the transduction of signals for growth and development from the cell surface to the nucleus. Members of the Raf family of kinases include Raf-1 which is ubiquitously expressed and A-Raf and B-Raf which have restricted patterns of expression. Raf kinases are believed to be key mediators of mitogenesis and differentiation, acting through a cascade of protein kinases that is also thought to be the pathway utilized by most oncogenes in cell transformation. (See Daum et al., *Trends Biochem Sci* 19:474–480, 1994 which is incorporated by reference.) The activation of Raf-1 in thought to involve phosphorylation of the molecule and several phosphorylation sites have been identified. (Morrison et al., *J Biol Chem* 268:17309–16, 1993 which is incorporated by reference). The phosphorylated Raf protein may then bind to the 14-3-3 protein which has been suggested to be essential to activation of Raf-1 in its mediation of these events inasmuch as microinjection of 14-3-3 results in Raf-1 activation and is required for function when Raf-1 is expressed in yeast (Fantl et al., supra; Li et al., *EMBO J* 14: 685–96, 1995; Irie et al., *Science* 265:1716–1719 which are incorporated by reference). It has been suggested that binding of 14-3-3 to Raf-1 is not necessary for activation, inasmuch as another group of investigators have reported that mutant forms of Raf-1 that are unable to bind to the 14-3-3 protein nevertheless show in vitro kinase activity as well as the ability to induce meiotic maturation in oocytes thus suggesting that binding to 14-3-3 is not essential (Michaud et al., *Mol Cell Biol* 15:3390–3397, 1995 which is incorporated by reference). This work is based upon the idea that 14-3-3 binds to a phosphorylation site (ser-259) that is induced by growth factor treatment. But 14-3-3 is associated with Raf-1 constitutively so this phosphorylation site (ser-259) cannot be the only binding site for 14-3-3. Thus, it was not appreciated that 14-3-3 binds to a Raf-1 phosphorylation site that is essential for function as is disclosed herein.

Nevertheless, because of the role of Raf-1 and possibly also the 14-3-3 proteins in a disease process involving growth and differentiation, in particular such conditions as cancer, atherosclerosis and autoimmune disease, it would be desirable to provide a method for interrupting this signal transduction pathway and thereby provide a new approach to treating these diseases.

BRIEF DESCRIPTION OF THE INVENTION

Accordingly, the inventors herein have succeeded in devising novel compositions and methods that act to inhibit the activation of a signal transducing protein by 14-3-3 protein by binding to the 14-3-3 protein and thereby prevent its binding to the signal transducing protein and its subsequent activation. Because the 14-3-3 proteins are utilized in a ubiquitous manner in the activation of signal transducing proteins, the present methods and compositions are applicable to a wide variety of such signal transducing proteins.

In one embodiment, the present invention provides a composition comprising an isolated phosphoserine-containing peptide comprising the amino acid sequence Arg-Ser-$Xaa_1$-$Xaa_2$-$Xaa_3$-Pro where $Xaa_1$ is any amino acid, $Xaa_2$ is a phosphorylated serine and $Xaa_3$ is any amino acid (SEQ ID NO: 1). This sequence is based upon the amino acid residues surrounding both the Serine-259 (residues 256–261) and Serine-621 (residues of 618–623) of Raf-1. More particularly, peptides within the scope of this invention can contain the Serine-259 specific amino acid sequence Arg-$Xaa_1$-Arg-Ser-$Xaa_2$-$Xaa_3$-$Xaa_4$-Pro where $Xaa_1$ and $Xaa_2$ are any amino acid, $Xaa_3$ is a phosphorylated serine and $Xaa_4$ is any amino acid (SEQ ID NO: 2) or the Serine 621 specific amino acid sequence Lys-$Xaa_1$-$Xaa_2$-Arg-Ser-$Xaa_3$-$Xaa_4$-$Xaa_5$-Pro where $Xaa_1$, $Xaa_2$ and $Xaa_3$ are any amino acid, $Xaa_4$ is a phosphorylated serine and $Xaa_5$ is any amino acid (SEQ ID NO: 3). Peptides containing these sequences specifically bind to the 14-3-3 protein preventing the activation of a protein of the Raf-1 family of kinases that are signal transducing proteins. Other suitable peptides can be designed containing all or part of the 6 amino acids of SEQ ID NO: 1 so long as the $Xaa_2$ is a phosphorylated serine and the peptides are capable of binding to a 14-3-3 protein that activates a member of the Raf-1 family of signal transducing proteins. Similarly, such other suitable peptides which are capable of binding to a 14-3-3 protein that activates a Raf-1 family member can contain all or part of SEQ ID NO:2 or SEQ ID NO:3 so long as they contain a phosphorylated serine. Peptides containing 6 amino acids corresponding to SEQ ID NO: 1 in which the serine in position $Xaa_2$ is not phosphorylated show little or no capacity to bind to isoforms of the 14-3-3 protein.

Both peptide and non-peptide derivatives of the peptides can also be prepared that exhibit the functionality of being capable of binding to the 14-3-3 protein and blocking the binding of 14-3-3 to the signal transducing protein to inhibit its signal transducing properties in a cell.

In another embodiment, a method is provided for inhibiting the intracellular activation of a signal transducing protein by administering to a cell an effective amount of a peptide that contains the amino acids sequences as set forth in SEQ ID NO: 1 or SEQ ID NO: 2 or SEQ ID NO: 3 or a derivative thereof wherein the peptide or derivative thereof binds to a 14-3-3 protein. The administering of the exogenous peptide or derivative thereof to a cell and the binding of the peptide to the 14-3-3 protein blocks the binding of 14-3-3 to the signal protein resulting in inhibition of the signal transducing activity of the protein.

In another embodiment, a method is provided for identifying a substance that binds to a 14-3-3 protein and thereby inhibits the activity of a signal transducing protein. The method comprises forming a mixture comprising a construct containing a 14-3-3 protein or derivative thereof immobilized to a substrate, a labeled peptide containing a sequence obtained from a Raf-1 sequence surrounding serine-259 or serine-621, and said pharmacologic agent. The mixture is then incubated under conditions under which the labeled peptide can bind to the construct but for the presence of the pharmacologic agent. The binding of the labeled peptide is then determined wherein a decrease in binding of the labeled peptide indicates a binding of the pharmacologic agent to the construct. Also included within the scope of the present invention is the pharmacologic agent identified by this method. The method can also be used to isolate the pharmacologic agent such as from a library of chemical substances.

Among the several advantages found to be achieved by the present invention, therefore, may be noted the provision of a composition which blocks the effects a growth factor or oncogene by binding 14-3-3 and inactivating or preventing the activation of the signal transducing protein, Raf-1; the provision of a method for blocking the intracellular activation of a signal transducing protein by administering to a cell an effective amount of a composition that binds to 14-3-3 protein; the provision of a method for identifying and/or isolating a pharmacologic agent that binds to 14-3-3 and inhibits the activation of Raf-1; and the provision of pharmacologic agents identified and/or isolated by said method.

DETAILED DESCRIPTION OF THE INVENTION

Figure 1:
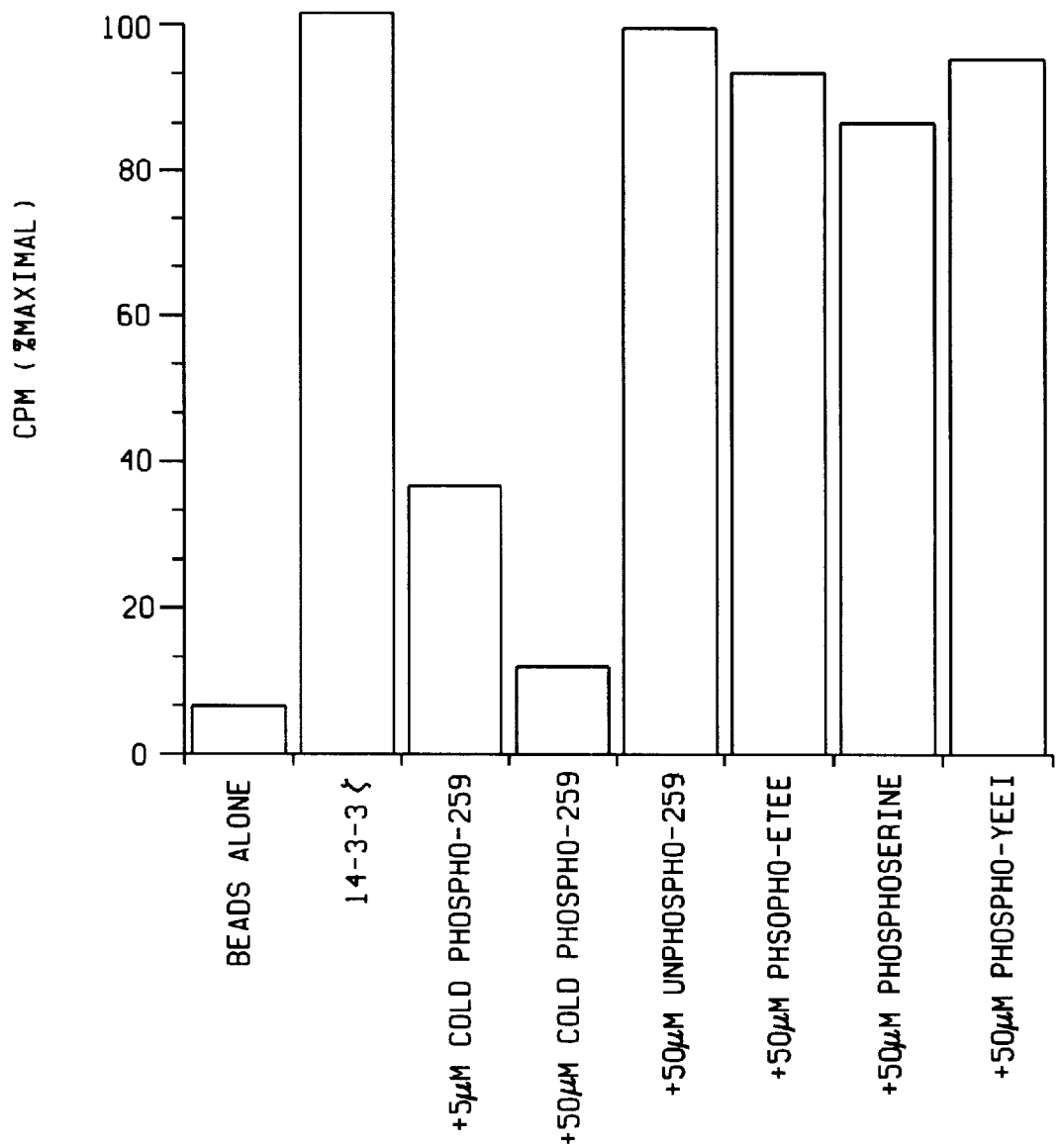
FIG. 1 illustrates the binding, measured by scintigraphy, of the Raf-259 peptide (SEQ ID NO: 4), which has been radiolabeled and phosphorylated, to immobilized GST/14-3-3 zeta in the absence or presence of different concentrations of cold phosphorylated non-radiolabeled wild-type Raf-259 peptide (cold phospho-259, SEQ ID NO: 5), non-phosphorylated and non-radiolabeled wild-type Raf-259 peptide (unphospho-259, SEQ ID NO: 4), phosphorylated casein Kinase II substrate peptide, RRREEEpTEEE (phospho-ETEE, SEQ ID NO: 6), non-radiolabeled free phosphoserine (phosphoserine), or the tyrosine-phosphorylated peptide, pYEEISPAK, (phospho-YEEI, SEQ ID NO: 7).

In accordance with the present invention, it has been discovered that signal transducing proteins, in particular the Raf-1 family of signal transducing proteins can be inhibited by the administration of a composition containing a peptide with a phosphorylated serine residue. The composition is capable of binding to the 14-3-3 protein in the cell. Administration of the peptide results in the blocking of the cellular effect of activation of the Raf-1 signal transducing protein by a substance such as a growth factor or an oncogene.

The process of identifying and preparing peptides containing a phosphorylated serine residue in which the peptide is capable of binding to 14-3-3 protein and inactivating a specific signal transducing protein is exemplified below for the isolation of the peptides that bind 14-3-3 and thereby inactivate the Raf-1 family of kinases. By inactivation it is meant that the protein or complex of proteins capable of signal transduction is either not produced or once produced, it is altered in such a manner that it is no longer capable of signal transduction.

Although it had been reported that the serine residues at positions 259 and possibly also position 621 of Raf-1 may be required for Raf-1 to bind to 14-3-3 protein and that dephosphorylated Raf-1 is unable to bind to 14-3-3 (Michaud et al. supra), nevertheless, the essential requirement for the binding of 14-3-3 protein to phosphoserines at position 259 and more particularly at position 621 of Raf-1 in the activation of Raf-1 was not appreciated. The present invention is based upon the heretofore unrecognized direct and specific interaction of 14-3-3 protein with phosphoserine-containing peptides derived from a Raf-1 sequence surrounding the serine-259 and, more particularly, the serine-621.

One composition of the present invention comprises a peptide that includes a sequence of 6 amino acids that comprises Arg-Ser-Xaa$_1$-Xaa$_2$-Xaa$_3$-Pro where Xaa$_1$ is any amino acid, Xaa$_2$ is phosphorylated serine and Xaa$_3$ is any amino acid (SEQ ID NO: 1). It has been found that a peptide molecule containing this sequence is capable of directly and specifically binding to 14-3-3 protein blocking activation of Raf-1 signalling. This 6 amino acid sequence corresponds to the sequence of amino acids 256–261 (Arg-Ser-Thr-Ser-Thr-Pro, SEQ ID NO: 8) and amino acids 618–623 (Arg-Ser-Ala-Ser-Glu-Pro, SEQ ID NO: 9) of Raf-1 except that the serine in position 259 or 621 is phosphorylated. By phosphorylating the serine residue in the amino acid sequence of SEQ ID NO: 8 or SEQ ID NO: 9, the phosphorylated peptide becomes capable of specific binding with 14-3-3 protein in the cell.

The novel peptides within the scope of the present invention can also contain the Serine-259, Raf-1 derived amino acid sequence Arg-Xaa$_1$-Arg-Ser-Xaa$_2$-Xaa$_3$-Pro where Xaa$_1$ is any amino acid, Xaa$_2$ is a phosphorylated serine and Xaa$_3$ is any amino acid (SEQ ID NO: 2) or the Serine 621, Raf-1 derived amino acid sequence Lys-Xaa$_1$-Xaa$_2$-Arg-Ser-Xaa$_3$-Xaa$_4$-Pro where Xaa$_1$ is any amino acid, Xaa$_2$ any amino acid, Xaa$_3$ is a phosphorylated serine and Xaa$_4$ is any amino acid (SEQ ID NO: 3).

The novel peptides of the present invention can also comprise other peptides that are longer than SEQ ID NOS: 1–3 in which additional amino acids have been added to either of the terminal amino acids so long as the resulting peptide remains capable of binding to the 14-3-3 protein. Other such exemplary peptides suitable for binding to a 14-3-3 protein and blocking Raf-1 signal transducing activity include a 15 amino acid peptide based upon the sequences surrounding serine-259 of Raf-1, i.e., Leu-Ser-Gln-Arg-Gln-Ser-Thr-Xaa-Thr-Pro-Asn-Val-His-Ala where Xaa is a phosphorylated serine (SEQ ID NO: 5) and the sequences surrounding serine-621 of Raf-1, Leu-Pro-Lys-Ile-Asn-Arg-Ser-Ala-Xaa-Glu-Pro-Ser-Leu-His-Arg where Xaa is a phosphorylated serine (SEQ ID NO: 10). In addition, certain amino acids with SEQ ID NO: 1 can be replaced with other amino acids so long as the phosphoserine is retained. Preferably, peptides prepared in accordance with the present invention are between six and about thirty amino acids in length. The peptides can be derived from the Raf-1 molecule or they can be an unrelated sequence provided that the six amino acid sequence of SEQ ID NO: 1 is included in the peptide or is similar to the sequence of SEQ ID NO: 1 maintaining that the serine in the amino acid sequence is phosphorylated.

In addition, modified serine residues such as phosphonoserines or serines with sulfur derivatives can also be used in place of phosphoserine as well as glutamic acid, which like the phosphoserine residue is negatively charged.

Included within the scope of peptides of the present invention are also sequences based upon paralogs and orthologs of Raf-1 and hybrid and modified forms of the peptides of the present invention in which certain amino acids have been deleted or replaced or modifications such as where one or more amino acids have been changed to a modified or unusual amino acid so long as the peptide retains the ability to bind to 14-3-3 protein and block the activation of Raf-1 by the 14-3-3 protein.

Based upon the results reported herein, the inventors believe that the Serine-621 of Raf-1 may be a more preferred binding site than the Serine-259 of Raf-1 for 14-3-3 protein when these serines are phosphorylated. Thus, the preferred peptides of the present invention are based upon the amino acids surrounding the Serine-621 of Raf-1.

The serine residue in the peptide sequences of the present invention can be phosphorylated by known methods. The peptide also can be produced by standard synthetic procedures such as by "classical" Merrifield method of solid phase peptide synthesis or by using the FMOC strategy on a RaMPS multiple peptide synthesis system (DuPont Co., Wilmington Del.) as described in Caprino and Han (*J Org Chem* 37:3404, 1972 which is incorporated by reference).

After a suitable peptide has been made, the peptide can be prepared in a pharmaceutically acceptable composition that is capable of delivering the peptide into to a cell. Any known and available means can be used for delivering the peptide into a cell. For example, the peptide may be incorporated with a carrier moiety such as a liposome that is capable of delivering the peptide into the cytosol of a cell. Such methods are well known in the art (for example see Amselem et al., *Chem Phys Lipids* 64:219–237, 1993 which is incorporated by reference). Alternatively, the peptide can be modified to include specific transit peptides that are capable of delivering the peptide into the cytoplasm of a cell or the peptide can be delivered directly into a cell by microinjection or delivery can be by intravenous administration in the intact individual in a pharmaceutically acceptable composition.

An effective amount of the peptide must be introduced into the cell so that binding to the 14-3-3 protein takes place. It is to be understood that the amount of peptide necessary to be introduced into any particular cell is dependent upon the cell, but can be determined using standard dose/response analysis.

Based on the structural features of the critical amino acid sequence of the peptides of the present invention that permit the binding of the peptide with the 14-3-3 protein, one can develop non-peptide derivatives that are capable of binding to the 14-3-3 protein. It is believed that at a minimum, non-peptide compositions that would be capable of binding to a 14-3-3 protein would contain a phosphorylated serine-like structure and would be capable of being introduced into a cell.

The techniques for development of peptide mimetics are well known in the art. (See for example, Navia and Peattie, *Trends Pharm Sci* 14:189–195, 1993; Olson et al., *J Med Chem* 36:3039–3049, 1993 which are incorporated by reference). Typically this involves identification and characterization of the protein target as well as the protein ligand using X-ray crystallography and nuclear magnetic resonance technology. In the case of 14-3-3 proteins, the complete sequence and the X-ray crystal structure for these proteins are known. Using information learned from the structure of the target protein and ligand peptide, a pharmacophore hypothesis is developed and compounds are made and tested in an assay system. An assay system based upon displacement of ligand from 14-3-3 protein can be used.

Thus, in another embodiment the peptide ligands of this invention are used to detect non-peptide compositions capable of binding to 14-3-3 peptide. A standard radioligand assay system can be used. (For example, see Bylund and Toews, *Am J Physiol* 265:L421–429, 1993 which is incorporated by reference). The method involves forming a mixture of a labeled peptide containing a sequence obtained from a Raf-1 sequence surrounding serine-259 or serine-621, a protein comprising at least a portion of a 14-3-3 protein capable of binding to the labeled peptide wherein the 14-3-3 protein is immobilized on a solid substrate, and a candidate compound. The labeled protein contains at least the 6 amino acids of SEQ ID NO: 1 and preferably about 15 amino acids in length. The labeled protein can also be the full length Raf-1 molecule or any portion thereof so long as the portion binds to the 14-3-3 protein.

The labeled protein can comprise any of a variety of labels known in the art. Typically a radiolabeled protein is used. The radiolabeled peptide can be prepared by attaching a radiolabeled group to the protein such as a phosphate group containing radiolabeled phosphorus or incorporation into the protein structure such as with a methionine residue containing radiolabeled sulfur. One radiolabeling method is illustrated in the examples below wherein the peptide is radiolabeled by phosphorylating the peptide using protein kinase A and [$^{32}$P]-γ-ATP. Radiolabeling can also be accomplished with a number of other known methods including using either $^{3}$H or $^{125}$I or biotinylation according to standard methods. For example, the Bolton Hunter Reagent can be used (ICN Chemicals, Radioisotope Division, Irvine, Calif.).

The composition of 14-3-3 to which the radioligand binds can be prepared by expression as a Glutathione-S-transferase 14-3-3 fusion protein in bacteria as discussed below. A standard ELISA-style plate assay can be used to bind radiolabeled ligand and then recover and measure the amount of bound ligand. (For example see Slack et al. *BioTechniques* 7:1132–1138, 1989; Dower et al, *J Immunol* 142:4314–4320, 1989 which are incorporated by reference). Competitive inhibition of the binding of the radiolabeled peptide ligand to the 14-3-3 protein on addition of a test compound can be evaluated by standard methods of analysis. (For example, see Rovati, *Pharmacol Res* 28:277–299, 1993 which is incorporated by reference). Alternatively, a non-radiolabeling method can be used to detect competitive displacement of the peptide ligand from the 14-3-3 protein. Such non-radiolabeling methods can utilize labels including enzymes, fluorescers, chemiluminescers, enzyme substrates or co-factors, enzyme inhibitors, particles, dyes and the like. Moreover, the assays can also be performed by using solid phase peptide and labeled forms of purified, recombinant 14-3-3 protein.

The peptides of the present invention are useful in blocking the activation of Raf-1 as a signal transducing peptide in response to cellular stimulation by insulin or a growth factor or in response to an oncogene product produced within the cell such as mutant Ras protein. Such blocking of signal transduction is likely to be particularly effective in treating tumors involving a mutant Ras protein or involving oncogenic activation which utilizes a Ras protein pathway. The requirement of Raf-1 activity for Ras effector signalling allows the peptides of the present invention to interrupt the Ras protein pathway of oncogenic activation in tumor cells. (see Prendergast et al., *BioEssays* 16:187–191, 1994 which is incorporated by reference).

Peptides and derivatives thereof prepared in accordance with the present invention can be used to inhibit the intracellular activation of Raf-1 in a mammalian cell and thereby provide a useful therapeutic composition for use in the treatment of diseases. Such diseases that can be advantageously treated have as a component of the disease an increased or inappropriate signal transduction mediated by Raf-1 such as, for example, in the treatment of cancer. In such treatments, it can be sometimes advantageous to target the peptides or derivatives of the present invention to the cancerous cells. Such specific targeting is well known within the art of cancer treatment and the preparation of suitable formulations and methods requires no more than routine experimentation.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

EXAMPLE 1

This example illustrates the direct binding of 14-3-3 zeta to a serine phosphorylated Raf-1 peptide.

A peptide containing a Raf-1 sequence surrounding serine-259 of Raf-1 (residues 251–265, LSQRQRSTSTPNVHM, SEQ ID NO: 4, designated Raf-259) was synthesized, purified, and analyzed according to methods previously described (Lorenz et al., 1988 which is incorporated by reference). Synthesis according to these methods was on either an ABI model 432A (Perkin/Elmer, Foster City, Calif.) or a Symphony/Multiplex synthesizer (Rainin Instrument Co, Woburn, Mass.) using standard FMOC chemistry. Reagents for peptide synthesis were purchased from ABI, Rainin, and Advanced ChemTech (Louisville, Ky.). Reagents for peptide synthesis were purchased from ABI, Rainin, and Advanced ChemTech (Louisville, Ky.). The peptide was purified by $C_{18}$ reverse phase HPLC and their identify confirmed and their concentration determined by amino acid analysis (Beckman Model 6300, Beckman Instruments, Palo Alto, Calif.). Peptides prepared by this method were shown to consist of a single species of the correct molecular weight by mass spectrometry (Washington University Mass Spectrometry Facility).

The 14-3-3 protein isoforms for use in binding studies with the above peptides were prepared as proteins fused with glutathione-S-transferase (GST) and immobilized to glutathione agarose beads. GST/14-3-3 fusion proteins were made by generating BamHI and EcoRI restriction endonuclease sites (underlined) at the 5' and 3' ends respectively of the 14-3-3 cDNAs by polymerase chain reaction (PCR) using the following isoform sequence specific pairs of primers: 14-3-3 beta, GA<u>GGATCC</u>ACAATGGATAAAAGTGAG (SEQ ID NO: 11), GA<u>GAATTC</u>TTAGTTCTCTCCCTCCCCA (SEQ ID NO: 12); 14-3-3 eta GA<u>GGATCC</u>GGGGACCGGGAGCAGCTG (SEQ ID NO: 13), GA<u>GAATTC</u>TCAGTTGCCTTCTCCTGC (SEQ ID NO: 14); 14-3-3 tau GA<u>GGATCC</u>GAGAAGACTGAGCTGATC (SEQ ID NO: 15), GA<u>GAATTC</u>TTAGTTTTCAGCCCCTTC (SEQ ID NO: 16); 14-3-3 zeta ATT<u>GGATCC</u>GATAAAAATGAGCTGGTTC (SEQ ID NO: 17), TTT<u>GAATTC</u>AATTTTCCCCTCCTTCTCCT (SEQ ID NO: 18). The cDNA products were digested with BamHI and EcoRI, subcloned into the vector pGEX-KT (Guan and Dixon, *Anal Biochem* 192: 262–7, 1991 which is incorporated by reference). The vector was used to transform the DH5α strain of *E. Coli*. GST-14-3-3 fusion protein expression in log-growth phase bacterial cultures was accomplished by induction with 100 μM isopropyl β-D-thiogalactopyranoside (IPTG; Gold Biotechnology, St. Louis) for 4 hours. Cells were disrupted by sonication and lysates, containing 1% Triton X-100, were incubated with glutathione agarose beads (Sigma, St. Louis) at 4° C. overnight. Fusion proteins were eluted by incubation with 10 mM reduced glutathione (Sigma, St. Louis) in phosphate buffered saline for 1 hour at room temperature, dialyzed in phosphate buffered saline and quantitated by Coomassie staining SDS polyacrylamine gels compared against bovine serum albumin standards.

The Raf-259 peptide (SEQ ID NO: 4) was phosphorylated in vitro using protein kinase A (PKA) and [$^{32}$P]-γ-ATP following the manufacturers instruction (PKA, New England Biolabs) with 20 μCi of [$^{32}$P]-γ-ATP (NEN-Dupont, 6000 Ci/mmol). The efficiency of phosphorylation was calculated to be between 7 and 12% based upon the specific activity of the labelled peptide.

Figure 2:
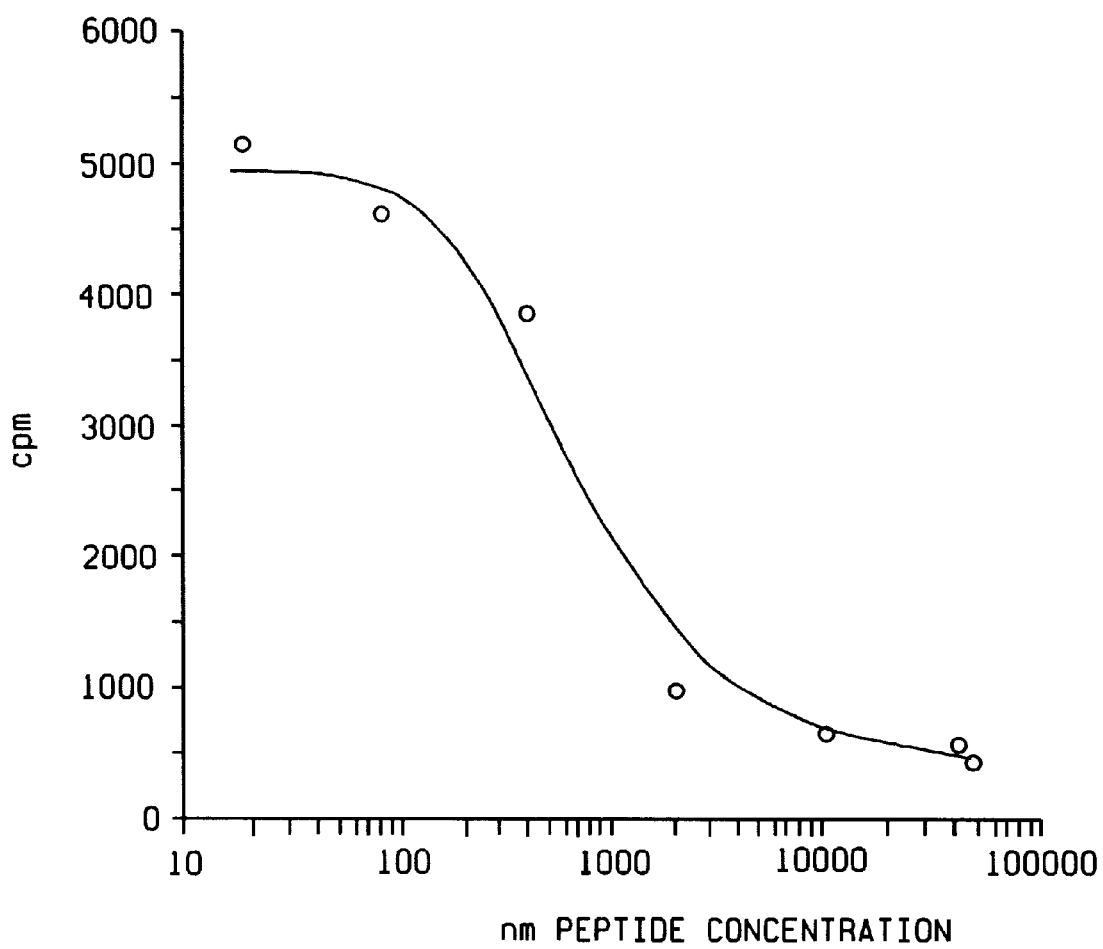
FIG. 2 illustrates the competitive displacement of the phosphorylated and radiolabeled wild-type Raf-1 peptide (SEQ ID NO: 4) from immobilized GST/14-3-3 zeta by non-radiolabeled, phosphorylated Raf-259 peptide (SEQ ID NO: 5) measured by scintigraphy.

The labeled peptide was then incubated with immobilized 14-3-3 zeta fusion protein and binding of the labelled peptide was measured. The results shown in FIG. 1 demonstrated that the labeled phosphorylated peptide bound to the 14-3-3 zeta coupled beads, but not to the glutathione beads alone. Binding was specific for phosphoserine because it could be displaced with phosphorylated peptide, but not with the unphosphorylated peptide. Binding was also sequence specific. Neither free phosphoserine nor a threonine phosphorylated casein kinase II substrate peptide (Arg—Arg—Arg—Glu—Glu—Glu-Xaa-Glu—Glu—Glu where Xaa is phosphorylated tyrosine, SEQ ID NO: 19) displaced the bound phosphorylated peptide nor did a tyrosine phosphorylated peptide (Xaa-Glu—Glu-Ile-Gln-Pro-Ala-Lys where Xaa is a phosphorylated tyrosine, SEQ ID NO: 20). The interaction of the phosphorylated peptide with 14-3-3 protein was also of high affinity having an IC$_{50}$ of approximately 1–2 μM for the phosphorylated peptide (FIG. 2). Because the calculated efficiency of in vitro phosphorylation of the peptide ranged between 7–12%, the true IC$_{50}$ was approximately 70–240 nM.

Surface plasmon resonance (SPR) was used to directly measure the affinity of the interaction of 14-3-3 zeta for the Raf-1 peptide. These experiments were performed using the BIAcore 2000 (Pharmacia). The basic principles and detection methods have been reviewed previously (Jonsson et al. *Biotech.* 11:620–7, 1991; Jonsson et al. *Ann Bio Clin* 51:19–26, 1993 which are incorporated by reference). In brief, 5 μl of the biotinylated raf-259 peptide (1 nM) was immobilized onto streptavidin-coated (SA5, Pharmacia) sensor chips at a flow rate of 5 μl/min at 25° C. This generally resulted in an RU value of 20–25 units. To phosphorylate the immobilized peptides, 5 U of PKA in a buffer containing 200 μM ATP in 50 μl was infused over the chip at a flow rate of 2 μl/min at 30° C.

Figure 3:
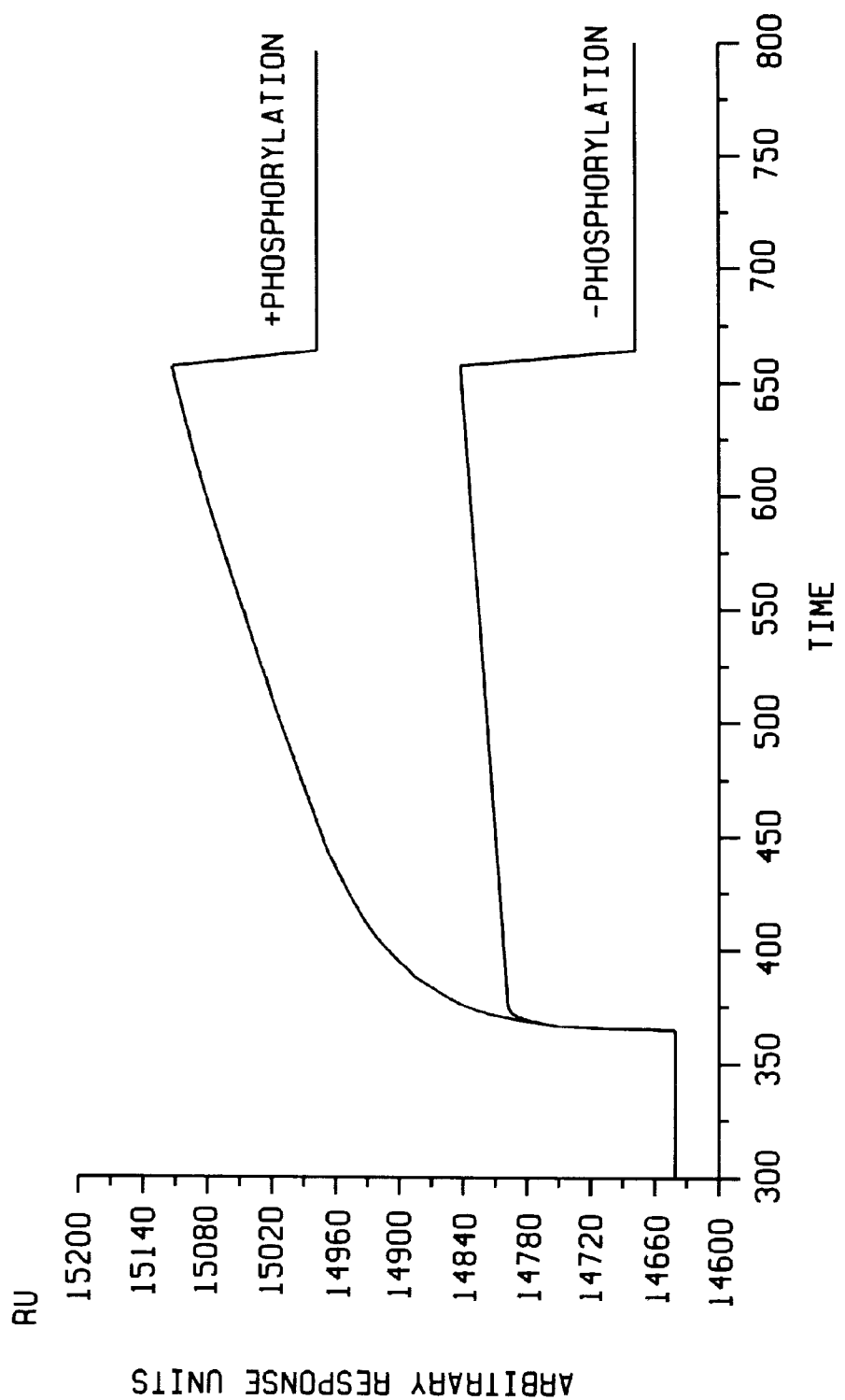
FIG. 3 illustrates the surface plasmon resonance assessment of peptide binding to 14-3-3 protein showing the binding of GST-14-3-3 zeta (1 $\mu$M) to phosphorylated biotinylated, Raf-1 peptide bound to a strepavidin coated sensor and lack of binding of the corresponding non-phosphorylated peptide.

When the unphosphorylated Raf-1 peptide (SEQ ID NO: 4) was attached to sensor surface and tested for its ability to bind injected 14-3-3 zeta, no significant binding was observed (FIG. 3). Following in situ phosphorylation of the peptide and re-injection of 14-3-3 zeta over the sensor surface, binding was clearly demonstrated (FIG. 3). This binding was specific to the 14-3-3 moiety as GST alone did not bind to either the unphosphorylated or phosphorylated peptide (data not shown).

Because the surface plasmon resonance detects binding in real time, this method can be used to directly determine the rates of association (k$_{on}$) and dissociation (k$_{off}$). For these kinetic measurements, GST/14-3-3 fusion proteins were injected over a range of concentrations between 200 nM and 5 μM. The "on" rate, k$_{on}$, was determined by calculating dR/dt for the initial linear portion of association using the Biaevaluation software (Pharmacia). Because ligand rebinding to the sensor chip can affect the "off" rate (k$_{off}$, Panayotou et al. *Mol Cell Biol* 13:3567–76, 1993 which is incorporated by reference), we measured the "off" rate in the presence of 50 μM free ligand by using the coinject function of the Biacore. The "off" rate measured in the absence of 50 μM free ligand was approximately 10-fold lower.

The biotinylated, unphosphorylated Raf-1 peptide (SEQ ID NO: 4) was coupled to avidin coated chip surface to study the kinetics of its binding to 14-3-3 zeta. The association rate was determined to be approximately 2.3×10$^4$ M$^{-1}$×s$^{-1}$ and the dissociation rate was determined to be approximately 2.8×10$^{-3}$ s$^{-1}$. To minimize the effects of protein rebinding to the surface of the sensor chip, the dissociation rate was measured in the presence of 50 μM free phosphorylated Raf-1 peptide. Given that the equilibrium dissociation constant, K$_D$, can be determined by K$_D$=k$_{off}$/k$_{on}$, the apparent K$_D$ measured by SPR is approximately 122 nM. These results show that 14-3-3 binds to the phosphoserine peptides of the present invention with high affinity.

EXAMPLE 2

This example illustrates the sequence specificity for the binding of the phosphoserine Raf-1 peptides to 14-3-3 proteins.

As the Raf-1 peptide used above (SEQ ID NO: 4) contains potential PKA phosphorylation sites at position 257 and 259, confirmation that phosphoserine-259 is the critical phosphorylated residue was required. Raf-259 peptides were, therefore, synthesized with phosphoserines at positions corresponding to position 257 (pS-Raf-257) (SEQ ID NO: 21), 259 (pS-raf-259)(SEQ ID NO: 5) or both 257 and 259 (pS-Raf-257, 259)(SEQ ID NO: 22). The peptides were synthesized according to the methods in Example 1 with the exception that the phosphoserine containing peptides were synthesized using FMOC-Ser(PO(OH,OBzl))—OH (NOVAbiochem, San Diego, Calif.) following the manufacturer's recommendations. Each of the peptides was purified by HPLC and the integrity of each peptide was confirmed by mass spectroscopy. The peptides were based upon sequences in Raf-1 surrounding serine-259 and serine 621 and are as shown in Table 1.

TABLE 1

| Sequence | | | | | | | | | | | | | | Name | SEQ ID NO: |
|---|---|---|---|---|---|---|---|---|---|---|---|---|---|---|---|
| L | S | Q | R | Q | R | S | T | S | T | P | N | V | H | M Raf-259 | 4 |
| L | S | Q | R | Q | R | pS | T | S | T | P | N | V | H | A pS-Raf-257 | 21 |
| L | S | Q | R | Q | R | S | T | pS | T | P | N | V | H | A pS-Raf-259 | 5 |
| L | S | Q | R | Q | R | pS | T | pS | T | P | N | V | H | A pS-Raf-257, 259 | 22 |
| L | S | Q | <u>A</u> | Q | <u>A</u> | S | T | pS | T | P | N | V | H | A 254/256RA | 26 |
| L | S | Q | <u>A</u> | Q | R | S | T | pS | T | P | N | V | H | A 254RA | 27 |
| L | S | Q | R | Q | <u>A</u> | S | T | pS | T | P | N | V | H | A 256RA | 28 |

TABLE 1-continued

| Sequence | | | | | | | | | | | | | Name | SEQ ID NO: |
|---|---|---|---|---|---|---|---|---|---|---|---|---|---|---|
| L | S | Q | A | Q | S | R | T | pS | T | P | N | V | H | A | R-2 | 29 |
| L | S | Q | A | R | Q | S | T | pS | T | P | N | V | H | A | R-4 | 30 |
| L | S | Q | R | Q | R | S | T | pS | T | A | N | V | H | M | PA | 31 |
| L | P | K | I | N | R | S | A | pS | E | P | S | L | H | R | pS-Raf-621 | 10 |

The ability of each peptide to inhibit binding of 14-3-3 zeta to the phosphorylated peptide was then tested in a range of concentrations between 1 and 50 μM. 14-3-3 zeta was prepared according to the methods in Example 1 and binding affinities and specificities were determined using the peptides in Table 2. The 14-3-3 zeta fusion proteins (0.5–1.0 μM) were pre-incubated with a given peptide at concentrations between 1 μM and 50 μM. 14-3-3 zeta was then infused across a sensor chip surface which had been previously coupled with the phosphorylated Raf-259 peptide (SEQ ID NO: 4). $IC_{50}$ values were determined by plotting the concentration of competitor peptide required to achieve a 50% reduction in equilibrium binding. Because concentrations of 14-3-3 were required (500–1000 nM) to reach equilibrium binding that were much higher than the apparent $K_D$ (100–150 nM), the $IC_{50}$ values that were derived provide only a relative affinity for the different peptides used (Payne et al., *Proc Natl Acad Sci USA* 90:4902–4906, 1993 which is incorporated by reference).

$IC_{50}$ values for the interaction of each of the labeled proteins with 14-3-3 zeta is shown in Table 2.

TABLE 2

| Peptide | SEQ ID NO | IC50(μM) | Peptide | SEQ ID NO | IC50(μM) |
|---|---|---|---|---|---|
| pS-Raf-259 | 5 | 6 | 256RA | 28 | 19 |
| pS-Raf-257 | 21 | >50 | R-2 | 29 | >50 |
| pS-Raf-257,259 | 22 | >50 | R-4 | 30 | 11 |
| 254/256RA | 26 | >50 | PA | 31 | 25 |
| 254RA | 27 | 9 | pS-Raf-621 | 10 | 1 |

The pS-raf-259 peptide (SEQ ID NO: 5) was found to compete with an $IC_{50}$ of approximately 6 μM (Tables 3 and 4). In contrast, the pS-raf-257 (SEQ ID NO: 21) peptide and the pS-raf-257,259 peptide (SEQ ID NO: 22) demonstrated little, if any, inhibition at the highest concentration tested, 50 μM. This demonstrates that phosphorylation of serine-259 is critical for 14-3-3 zeta binding. Furthermore, the inability of the pS-raf-257–259 (SEQ ID NO: 22) peptide to bind suggests that the serine at position 257 is also important. As the only difference between pS-raf-257 (SEQ ID NO: 21) and pS-raf-259 (SEQ ID NO: 5) peptides is the position of the phosphoserine, high affinity binding of 14-3-3 zeta to serine phosphate is exquisitely sequence specific.

To further define the 6 amino acid binding motif (SEQ ID NO: 1), sequences similar to the amino acids surrounding serine-259 in other proteins known to bind 14-3-3 were identified (Table 3). Interestingly, CDC25 shares the motif Arg-Xaa$_1$-Arg-Ser-Xaa$_2$-Ser-Xaa$_3$-Pro (where Xaa$_1$, Xaa$_2$ and Xaa$_3$ are any amino acid) (SEQ ID NO: 23) while polyoma middle T antigen contains a slightly shorter version of the motif (Arg-Ser-Xaa$_1$-Ser-Xaa$_2$-Pro) (SEQ ID NO: 24). Surprisingly, Raf-1 contains both instances of the motif, at positions 256–261 and 618–623 respectively; both are known to be phosphorylation sites in vivo (Morrison et al., supra). This suggested that the binding motif is related to the sequence Arg-Xaa$_1$-Arg-Ser-Xaa$_2$-Xaa$_3$-Xaa$_4$-Pro (where Xaa$_1$ and Xaa$_2$ are any amino acid, Xaa$_3$ is phosphoserine and Xaa$_4$ is any amino acid) (SEQ ID NO: 25).

TABLE 3

SUBSTANCES KNOWN TO BIND 14-3-3

| SUBSTANCE | MOTIF | SEQ ID NO |
|---|---|---|
| Raf-1 (254-261) | RSTSTP | 39 |
| Raf-1 (616-623) | RSASEP | 40 |
| B-RAF (241-248) | RSSSAP | 41 |
| B-RAF (605-621) | RSASEP | 40 |
| Polyoma Middle T (268-275) | RSHSYP | 42 |
| CDC25B (301-308) | RSPSMP | 43 |
| PKC-epsilon | RSKSAP | 44 |
| PKC-gamma | RSPSSP | 45 |
| BCR (368-373) | RSQSQN | 46 |
| tyrosine hydroxylase | RHASSP | 47 |

TABLE 4

PUTATIVE PHOSPHORYLATED LIGANDS FOR 14-3-3

| SUBSTANCE | MOTIF | SEQ ID NO |
|---|---|---|
| A-RAF (206-213) | RSTpSTP | 39 |
| A-RAF (574-581) | RSApSEP | 40 |
| Bad | RSRpSAP | 48 |
| Mos | RSCpSIP | 49 |
| CDC25C (208-215) | RSPpSMP | 43 |
| Glucocorticoid Receptor | RSTpSRP | 50 |
| KSR-1 | RSPpSFP | 51 |
| PLC-gamma | RSEpSSP | 52 |
| p85 subunit of PI-3 kinase | RSPpSIP | 53 |
| PTP-MEG | RSPpSKP | 54 |
| PTP-epsilon | RSPpSGP | 55 |
| PTP-mu | RSVpSSP | 56 |
| SNF1 | RSRpSYP | 57 |
| 5'AMP Kinase | RSQpSKP | 58 |

The importance of the arginine residues in defining the 14-3-3 zeta binding motif was tested by synthesizing phosphopeptides with alanines substituted for either or both arginines (254/256RA, SEQ ID NO: 26; 254RA, SEQ ID NO: 27; and 256RA, SEQ ID NO: 28 according to Table 1). As shown in Table 2, the peptide with alanine substituted for both arginines (254/256RA, SEQ ID NO: 26) exhibited no detectable inhibition at concentrations up to 50 μM demonstrating that one or both arginine residues are critical for binding. The 254RA (SEQ ID NO: 27) peptide competed almost as efficiently as wild-type (9 μM) while the 256RA peptide (SEQ ID NO: 28) competed much less efficiently. Although this demonstrated that the arginine in position −3 from the phosphoserine is critical for binding, the inability of the alanine substitution at −5 to completely abrogate binding suggested that basic residues in other positions might also contribute to the binding affinity. The relative affinities of two additional peptides with the arginine placed in the −2 or −4 positions were therefore analyzed. The peptide with arginine in the −2 position (R-2, SEQ ID NO:

29) did not compete for binding at the highest concentration tested (50 μM) confirming that the position of the arginine residue is clearly important. However, the peptide with arginine in the −4 position (R−4, SEQ ID NO: 30) competed almost as well as the peptide with arginine in the −3 position (254RA, SEQ ID NO: 28). We concluded that an arginine residue is required in the −3 and/or −4 position from the phosphorylated serine.

To determine the importance of the proline residue, another phosphorylated peptide with alanine substituted for proline (PA) was generated (SEQ ID NO: 31). The PA peptide demonstrated an $IC_{50}$ of approximately 25 μM confirming that the proline residue is important but also suggesting that this position may tolerate other residues (Table 2).

To determine whether other predicted sequences containing the motif could bind 14-3-3, we tested a phosphopeptide corresponding to Raf-1 residues 613–627 (pS-raf-621, SEQ ID NO: 10). The $IC_{50}$ of this peptide was approximately 1 μM. The ability of the phosphorylated raf-621 peptide to bind at high affinity confirmed that the motif can be used to predict other proteins that bind 14-3-3. Its affinity, which is six times higher than that of the raf-259 peptide (SEQ ID NO: 5) also indicated that ser-621 of Raf-1 is the preferred binding site for 14-3-3 in contrast to what has been previously reported (Michaud et al., supra). As this latter peptide contains only one of the two N-terminal arginine residues, the minimal binding sequence for 14-3-3 zeta is Arg-Ser-$Xaa_1$-$Xaa_2$-$Xaa_3$-Pro where $Xaa_1$ is any amino acid, $Xaa_2$ is phosphoserine, and $Xaa_3$ is any amino acid (SEQ ID NO: 1).

Comparison of proteins known to bind 14-3-3 demonstrated that many contain sequences similar to those surrounding serine-259 of Raf-1 (Table 1). This analysis allowed us to deduce a putative motif for 14-3-3 binding as being Arg-Ser-$Xaa_1$-Ser-$Xaa_2$-Pro where $Xaa_1$ and $Xaa_2$ are any amino acid (SEQ ID NO: 1). The integrity of this derived motif was tested by using a series of alanine substituted phosphorylated peptides, a panel of degenerate peptides, as well as by testing whether 14-3-3 could bind to a peptide from a predicted site. The carboxy-terminal proline and the amino-terminal arginine residues were important for binding. Although analysis of the position dependence of the arginine demonstrated high affinity binding in either the −3 and −4 positions, the −3 position is required for phosphorylation by protein kinases. We believe, therefore, that arginine in the −3 position is the critical determinant for 14-3-3 binding in vivo.

The inability of the doubly phosphorylated peptide, pS-Raf-257,259 (SEQ ID NO: 22), to bind 14-3-3 suggested that the serine residue in the −2 position is also important. Experiments with degenerate peptides confirmed that specificity is conferred by residues in the −2 as well as the −3 and +2 positions relative to the phosphoserine. It is possible that other residues can substitute for the arginine, serine and proline inasmuch as other proteins known to bind 14-3-3 like bcr and tyrosine hydroxylase contain related sequences (Table 3) but do not contain the exact motif. An improved definition of the motif will be critical in the identification of other novel phosphoserine containing peptides based upon proteins that putatively bind 14-3-3 (represented in Table 4 in phosphorylated form).

Our data suggests that other proteins containing the motif, if appropriately phosphorylated, might bind 14-3-3. The SWISS-PROT protein database was, therefore, searched for eukaryotic proteins that contain the sequence Arg-Ser-$Xaa_1$-Ser-$Xaa_2$-Pro where $Xaa_1$ and $Xaa_2$ are any amino acid (SEQ ID NO: 32). As expected, c-Raf-1, CDC25 and polyoma middle T antigen were identified. Kinases closely related to c-Raf-1 like A-Raf-1, B-Raf-1, mos, mil and MEKK also contain the motif. Some additional proteins that contain the motif are shown in Table 4.

Based upon these results, the inventors herein believe that the primary 14-3-3 binding site on Raf-1 may not be Ser-259 as proposed previously (Michaud et al, supra), but rather Ser-621. Ser-259 phosphorylation is induced only after growth factor stimulation but 14-3-3 is bound constitutively to Raf-1 in unstimulated cells (Li et al. supra; Dent et al., Science 268:1902–6, 1995 which are incorporated by reference). Therefore, it is not likely that Ser-259 is the primary binding site of Raf-1 in vivo. Ser-621, a Raf 1 site which is constitutively phosphorylated (Morrison et al., supra), is, therefore, the preferred 14-3-3 binding site. Michaud et al. suggested serine-259 as the major binding site, because baculovirus expressed protein is aberrantly phosphorylated at both serine-259 and serine-621 (Morrison et al., supra).

Binding of 14-3-3 may not directly activate Raf-1 per se as Raf-1/14-3-3 complexes are present in unstimulated cells (Li et al., supra). But mutation of serine-621 in Raf-1 inhibits the association of 14-3-3 (Michaud et al., supra) and renders the kinase inactive. 14-3-3 binding to serine-621 is, therefore, believed to be required for Raf-1 kinase activity. Although the inventors herein do not intend that this invention be limited in any way by a particular mechanism of action, one possible explanation for the results reported herein is that 14-3-3 functions as a chaperone, to promote or stabilize an activatable conformation of Raf-1. This would explain why disruption of the 14-3-3/Raf-1 complexes with the phosphorylated peptide blocks Raf-1 activation. 14-3-3 interactions with phosphorylated serine-259 after growth factor treatment may also be important as serine-259 is required for PKC activation of Raf-1 (Kolch et al., Nature 364:249–252, 1993 which is incorporated by reference).

EXAMPLE 3

This example confirms the critical motif residues required for binding to 14-3-3 protein using degenerate peptides based upon Serine-621 of Raf-1.

A series of degenerate peptides based upon phosphoserine Raf-621 peptide (SEQ ID NO: 10) were synthesized to confirm that the arginine in the −3 position, the serine in the −2 position and the proline in the +2 position were the critical motif residues (Table 5). Six pools of peptides were synthesized with all twenty amino acids placed in positions −5, −3, −2, −1, +1 and +2 respectively. Each pool of twenty peptides was tested as competitive inhibitors for binding. We reasoned that if a particular position is not critical for binding, the pool of twenty peptides should compete as well as wild-type peptide for binding. On the other hand, if a particular amino acid is required at a particular position, only a small fraction of the pool will be able to compete for binding, thus increasing (up to 20 fold) the concentration of peptide needed to inhibit binding. Pools with degenerate amino acids in positions −5, −1 and +1 competed as well as wild-type demonstrating that these position are not critical for binding. As expected, pools with degenerate amino acids in position −3, −2 and +2 were weaker inhibitors of binding confirming that these are the critical positions.

TABLE 5

PEPTIDE IC50 (µM)

| Isoform | PA | RA | pS-Raf-259 | pS-Raf-257,259 | pS-Raf-257 | pS-Raf-621 |
|---|---|---|---|---|---|---|
| zeta | 25 | >50 | 6 | >50 | >50 | 1 |
| eta | 20 | >50 | 5 | >50 | >50 | 3 |
| beta | 24 | >50 | 6 | >50 | >50 | 2 |
| tau | 27 | >50 | 5 | >50 | >50 | 2 |

EXAMPLE 4

This example demonstrates that the phosphoserine Raf-1 peptides bind to different isoforms of 14-3-3 with the same affinity and specificity.

There are seven known isoforms of 14-3-3 which form homo- and heterodimers in vivo. If different isoforms of 14-3-3 could bind to proteins with distinct specificities, heterodimeric forms of 14-3-3 might function as modular linker proteins, bringing together different proteins into a single complex. We were, therefore, interested in determining whether different 14-3-3 isoforms recognize phosphoserine in a sequence specific fashion. This hypothesis was tested by expressing and purifying three other 14-3-3 isoforms, eta, beta and tau, and measuring their affinity towards the panel of phosphorylated peptides generated above. Using the Surface Plasmon Resonance method, the "on" and "off" rates for 14-3-3 binding to the phosphorylated Raf-259 peptide were calculated (Table 6). All four isoforms demonstrated very similar apparent binding affinities.

TABLE 6

| Isoform | $k_{on}(10^4 M^{-1} s^{-1})$ | $k_{off}(s^{-1})$ | $K_D(nM)$ |
|---|---|---|---|
| zeta | 2.30 | 0.0028 | 122 |
| eta | 2.26 | 0.0029 | 128 |
| beta | 2.20 | 0.0032 | 145 |
| tau | 2.50 | 0.0036 | 144 |

Competitive inhibition with the mutated phosphorylated Raf-1 peptides was used to determine whether their specificities were similar (Table 7). In each case, the calculated $IC_{50}$s were very similar to those calculated for 14-3-3 zeta. All four 14-3-3 isoforms exhibited little to no affinity towards the RA peptide and intermediate affinities towards the PA peptide.

These results suggest that the binding affinity and sequence specificity of multiple 14-3-3 isoforms for serine phosphorylated peptides are very similar suggesting that the peptides disclosed herein will inhibit the signalling functions of all isoforms of 14-3-3.

EXAMPLE 5

This example demonstrates that 14-3-3 protein can block dephosphorylation of Raf-1.

To confirm that 14-3-3 physically contacts the phosphoserine residue, we tested whether addition of 14-3-3 could block the ability of the serine/threonine phosphatase, PP1, to dephosphorylate Raf-1. One µg of GST-raf fusion protein adsorbed to glutathione agarose beads was phosphorylated in vitro with purified bovine PKA (Sigma) and [$^{32}$P]-γ-ATP. Ten µg of purified GST-14-3-3 β or a GST-P56-lck SH2 (Santa Cruz Biotechnology, Santa Cruz, Calif.) domain was added to the phosphorylated Raf fusion protein in PBS and incubated at room temperature for 1 hour. The beads were collected by centrifugation, resuspended in 25 µl buffer containing 50 mM Tris-HCl (pH 7), 0.1 mM EDTA, 5 mM DTT, 0.2 mM MnCl$_2$, 200 mg/ml bovine serum albumin and 1 U of recombinant protein phosphatase 1 (New England BioLabs, Beverly, Mass.) and incubated for 1 hour at 37° C. Proteins were analyzed by PAGE and quantitated using a phosphorimager (Molecular Dynamics, Sunnyvale, Calif.).

Figure 4:
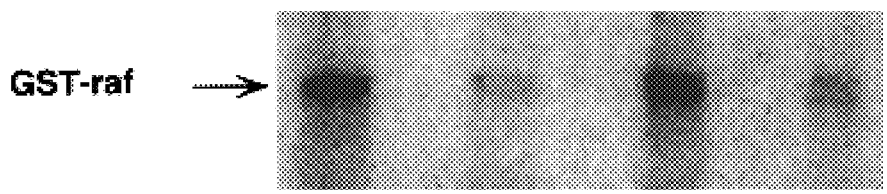
FIG. 4 illustrates the inhibition of dephosphorylation of Raf-1 by 14-3-3 showing (A) the phosphorylated GST-Raf fusion protein band on 10% acrylamide SDS gel analyzed by autoradiography (lane 1); absence of the same band on incubation with the serine/threonine phosphatase, PP1 (lane 2); presence of the band indicating inhibition of dephosphorylation in the presence of 14-3-3 protein (lane 3); and absence of the band with the control fusion protein GST-p56-lck and (B) the phosphorimager quantitation of results depicted in panel A.
Figure 4:
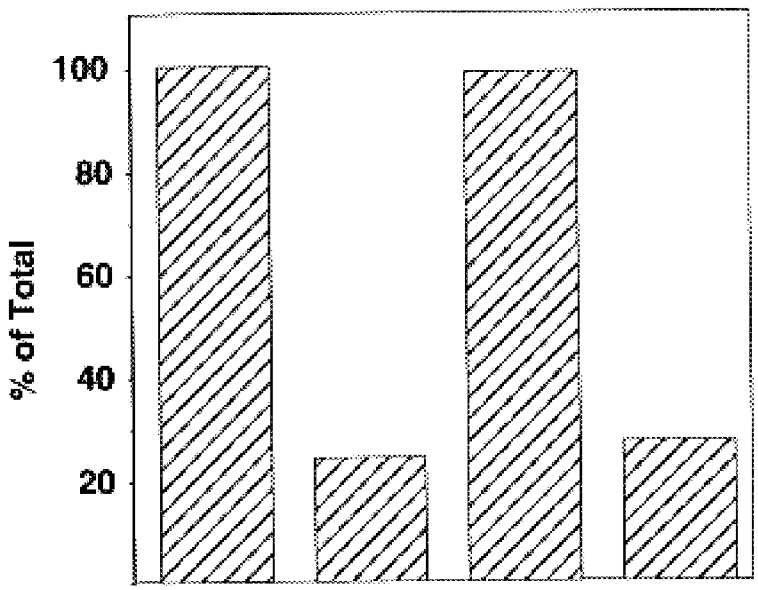

Incubation of phosphorylated Raf-1 with 14-3-3 completely blocked the ability of PP1 to dephosphorylate Raf-1 (FIG. 4). This was specific to 14-3-3 because addition of a control fusion protein, GST-p56-lck SH2, had no effect on the ability of PP1 to dephosphorylate Raf-1.

EXAMPLE 6

This example demonstrates that the Raf-1 phosphoserine peptides inhibit the 14-3-3/Raf-1 interaction in vitro.

The ability of phosphorylated peptides of the present invention to block 14-3-3/Raf-1 complex formation was tested as follows.

NIH 3T3 cells and T cell hybridoma (DO11.10) were washed twice in cold phosphate-buffered saline, lysed in cold NP40 lysis buffer (Muslin et al., *Mol Cell Biol* 13:4197–202, 1993 which is incorporated by reference) and cleared by centrifugation.

TABLE 7

| COMPETITOR PEPTIDE | | | | | | | | | | | | | | SEQ ID | % BINDING @ 10 µM |
|---|---|---|---|---|---|---|---|---|---|---|---|---|---|---|---|
| No peptide | | | | | | | | | | | | | | | 100% |
| pS-Raf-621 | L | P | K | I | N | R | S | A | pS | E | P | S | L | H | R | 10 | <5% |
| -5 | L | P | K | X | N | R | S | A | pS | E | P | S | L | H | R | 33 | <5% |
| -3 | L | P | K | X | N | X | S | A | pS | E | P | S | L | H | R | 34 | 17% |
| -2 | L | P | K | I | N | R | X | A | pS | E | P | S | L | H | R | 35 | 27% |
| +1 | L | P | K | I | N | R | S | X | pS | E | P | S | L | H | R | 36 | <5% |
| +1 | L | P | K | I | N | R | S | A | pS | X | S | L | H | R |   | 37 | <5% |
| +2 | L | P | K | I | N | R | S | A | pS | E | P | S | L | H | R | 38 | <56% |

The lysates prepared from NIH 3T3 cells were incubated for 1 hr at 4° C. with immobilized 14-3-3 in the presence or absence of phosphorylated and unphosphorylated Raf-1 peptides (SEQ ID NO: 5 and SEQ ID NO: 4, respectively). After washing three times in lysis buffer, Raf-1 binding was analyzed by immunoblotting using a polyclonal anti-Raf-1 antibody (Santa Cruz Biotechnology). In lane 1 lysate was added to immobilized 14-3-3 in the absence of added peptide. In lane 2 lysate was added to GST alone immobilized on glutathione-agarose. In lane 3 lysate was added to immobilized 14-3-3 in the presence of unphosphorylated Raf-259 peptide (SEQ ID NO: 4, 10 μM). In lane 4 lysate was added to immobilized 14-3-3 in the presence of phosphorylated pS-Raf-259 peptide (SEQ ID NO: 5, 10 μM).

Figure 5:
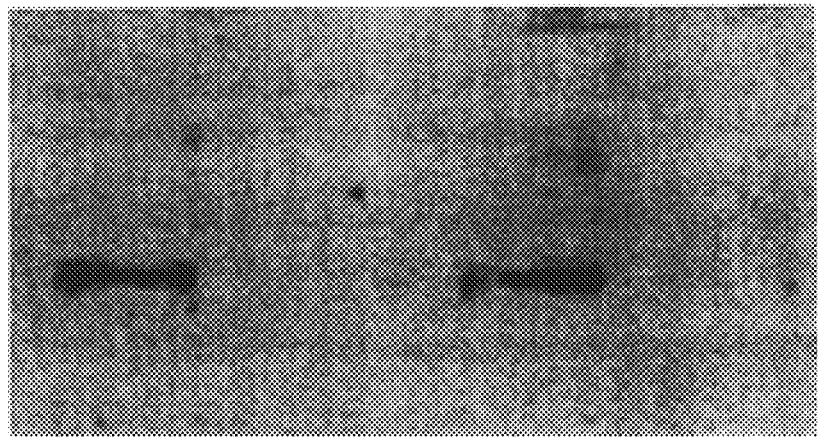
FIG. 5 illustrates the inhibition of 14-3-3/Raf-1 complex formation in vitro detected by immunoblotting using polyclonal anti-Raf-1 showing complex formation with GST-14-3-3 zeta immobilized on glutathione-agarose and NIH 3T3 cell lysate (lane 1), no complex formation with GST alone and lysate (lane 2), complex formation with GST-14-3-3 zeta, lysate, and non-phosphorylated Raf-259 peptide (SEQ ID NO: 4) (lane 3) and no complex formation with GST-14-3-3 zeta, lysate and phosphorylated Raf-259 peptide (SEQ ID NO: 5) (lane 4).

Incubation of 14-3-3 zeta with the phosphorylated raf-259 peptide (pS-raf-259)(SEQ ID NO: 5) completely inhibited its ability to bind Raf-1 (FIG. 5, lane 4). In contrast, incubation of cell lysates with the unphosphorylated Raf-1 peptide (SEQ ID NO: 4) had no effect on the ability of 14-3-3 zeta to bind to full-length Raf-1 (FIG. 5, lanes 3).

Figure 6:
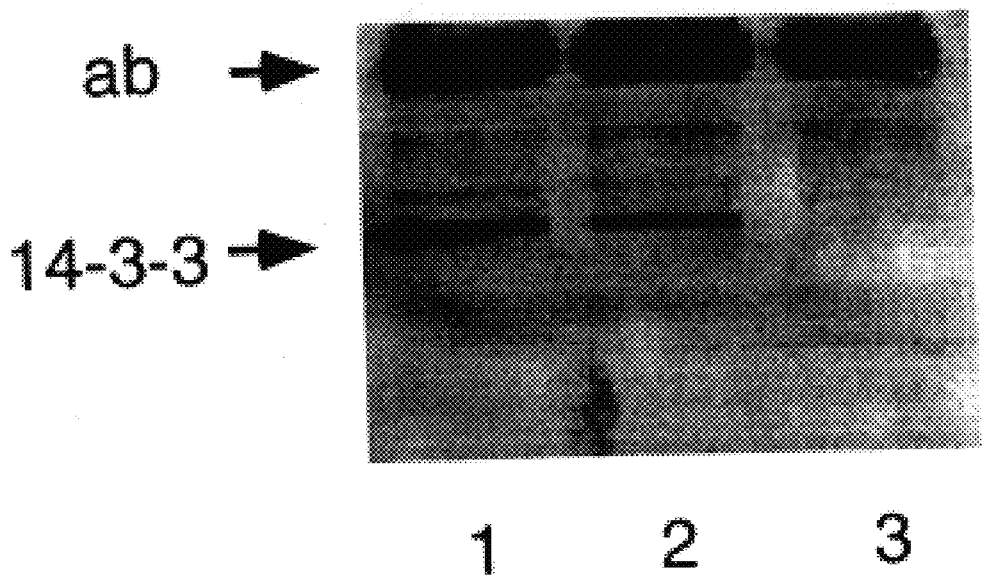
FIG. 6 illustrates disruption of pre-existing Raf-1/14-3-3 complexes in vitro using phosphorylated Raf-259 peptide (SEQ ID NO: 5: lane 2, 10 $\mu$M; lane 3, 100 $\mu$M) compared to the unphosphorylated Raf-259 peptide (SEQ ID NO: 4: lane 1, 100 $\mu$M).

The phosphopeptide could also promote the disassociation of preformed 14-3-3/Raf-1 complexes (FIG. 6). Either unphosphorylated or phosphorylated Raf-259 peptides (SEQ ID NO: 4 and SEQ ID NO: 5, respectively) were incubated with cell lysates prepared from a mouse T cell hybridoma for 1 hr at 4° C. Raf-1 immunoprecipitates were washed 3 times in lysis buffer and separated by SDS-PAGE. Associated 14-3-3 protein was detected by immunoblotting using a rabbit polyclonal anti-14-3-3 beta antibody (Santa Cruz Biotechnology; ab in FIG. 6). In lane 1 unphosphorylated Raf-259 peptide (SEQ ID NO: 4, 100 μM) was added to cell lysate. In lane 2 phosphorylated pS-Raf-259 peptide (SEQ ID NO: 5, 10 μM) was added to cell lysate. In lane 3 phosphorylated pS-Raf-259 peptide (SEQ ID NO: 5, 100 μM) was added to cell lysate.

Addition of the pS-Raf-259 peptide (SEQ ID NO: 5) at either 10 μM or 100 μM concentrations disassociated Raf-1/14-3-3 complexes (FIG. 6, lanes 2 and 3). Incubation of cell lysates with the unphosphorylated Raf-259 peptide (SEQ ID NO: 4) had no effect on Raf-1/14-3-3 complexes (FIG. 6, lane 1). The 14-3-3/Raf-1 complexes can, therefore, be disassociated by incubation with the phosphorylated Raf-1 peptide (SEQ ID NO: 5).

EXAMPLE 7

This example demonstrates that the Raf-1 phosphoserine peptides inhibit of 14-3-3/Raf-1 interaction in vivo in a model of oocyte maturation.

Phosphorylated Raf-1 peptides were microinjected into Xenopus oocytes. Because microinjection of 14-3-3 protein into frog oocytes activates Raf-1 inducing oocyte maturation (Fantl et al., supra), we reasoned that inhibition of 14-3-3 interactions using the phosphorylated Raf-1 peptides should block Raf-1 activation and subsequent oocyte maturation. Insulin was used to stimulate oocyte maturation and maturation was measured by assessing germinal vesicle breakdown (GVBD, Fabian et al., *J Cell Biol* 122:645–52, 1993; Muslin et al., supra which are incorporated by reference).

Large oocytes (Dumont stage VI) were removed from adult female frogs. Oocytes were manually dissected and collagenase treated. Oocytes were maintained in 1× modified Barth's saline with added bovine serum albumin, Ficoll 400, and antibiotics as described (Muslin et al., supra). Each oocyte was injected with 50 nmoles of peptide or with water. The final concentration of the peptide was estimated as 50 μM and the half-life measured as 15–20 minutes. Oocytes were treated with insulin (8.25 μg/ml) and incubated for 24 hours at 18° C.

Figure 7:
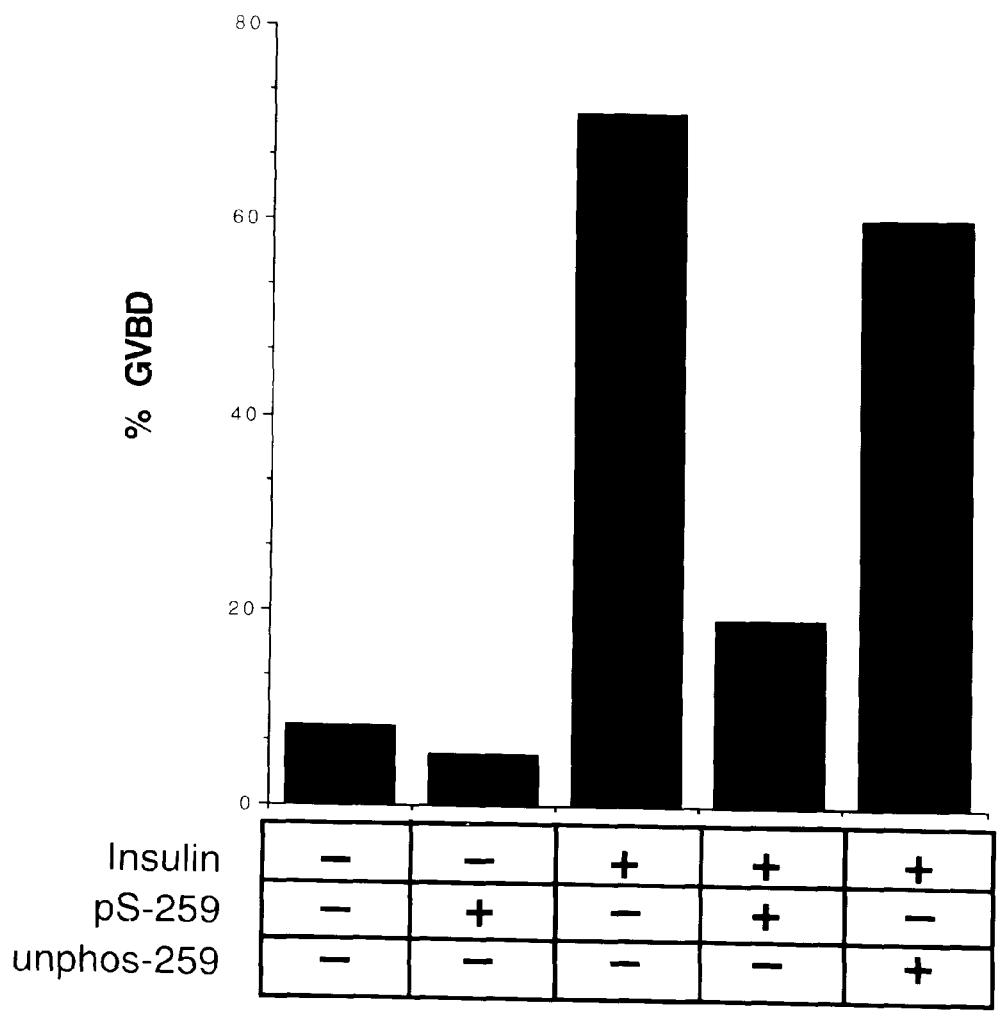
FIG. 7 illustrates the inhibition of germinal vesicle breakdown (GVBD) in Xenopus oocytes stimulated with insulin after microinjection of phosphorylated Raf-259 peptide (SEQ ID NO: 5) (pS-259) compared to no inhibition after microinjection of non-phosphorylated Raf-259 peptide (SEQ ID NO: 4) (unphos-259) or microinjection of water (-pS-259 and - unphos-259).

In the presence of insulin, microinjection of the phosphorylated Raf-259 peptide (SEQ ID NO: 5) but not the unphosphorylated Raf-259 peptide (SEQ ID NO: 4) inhibited insulin stimulated GVBD (FIG. 7). Consistent with this result, injection of the pS-Raf-621 peptide (SEQ ID NO: 10) significantly inhibited insulin stimulated GVBD but the RA peptide (SEQ ID NO: 26) did not (data not shown). These results demonstrate that phosphoserine Raf-1 peptides can inhibit oocyte maturation.

The mechanism of inhibition of oocyte maturation by the phosphoserine Raf-1 peptides was further elucidated by determining the effect of the phosphoserine-containing Raf-1 peptides on Raf-1 kinase activity in the insulin-treated oocytes.

Immature Xenopus oocytes were injected with phosphorylated or unphosphorylated peptide as above. Oocytes were stimulated with insulin for 24 hours and protein lysates were made. The oocytes were then lysed as described previously (Muslin et al., supra). Raf-1 immunoprecipitates were washed and then incubated in kinase buffer in the presence of 100 ng of recombinant polyhistidine-tagged MEK as a substrate as described (MacNicol et al., *Mol Cell Biol* 15: 6686–6693, 1995 which is incorporated by reference). The samples were then subjected to SDS-PAGE and the phosphorylated substrate was visualized by autoradiography.

Figure 8:
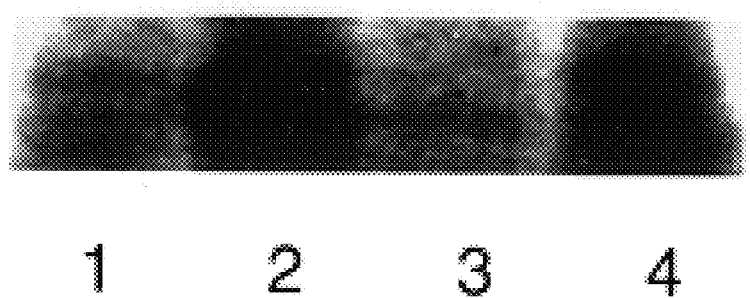
FIG. 8 illustrates the inhibition Raf-1 kinase activity by phosphorylated Raf-259 peptide showing no Raf-1 kinase activity in protein lysates made from oocytes not stimulated with insulin and microinjected with water (lane 1), no Raf-1 kinase activity in lysate from insulin-stimulated, water-injected oocytes (lane 2), no Raf-1 kinase activity in lysate from insulin-stimulated oocytes injected with phosphorylated Raf-259 peptide (lane 3), and Raf-1 kinase activity in lysate from insulin-stimulated oocytes injected with non-phosphorylated Raf-259 peptide (lane 4).

With reference to FIG. 8, lane 1 shows unstimulated water-injected oocytes; lane 2, insulin-stimulated water-injected oocytes; lane 3, insulin-stimulated oocytes injected with phosphorylated pS-Raf-259 peptide (SEQ ID NO: 5); and lane 4, insulin-stimulated oocytes injected with unphosphorylated Raf-259 (SEQ ID NO: 4).

Raf-immunoprecipitates from oocytes microinjected with the phosphorylated Raf-1 peptide, pS-Raf-259 (SEQ ID NO: 5), demonstrated little to no activation of Raf-1 kinase as compared with the oocytes mock-injected or injected with the unphosphorylated Raf-1 peptide (SEQ ID NO: 4) after insulin treatment. These results are consistent with previous work demonstrating that 14-3-3 is required for Raf-1 activation (Irie et al., *Science* 265:1716–1719, 1994; Freed et al., *Science* 265:1713–6, 1994; and Li et al., supra which are incorporated by reference).

EXAMPLE 8

This example illustrates the effectiveness of the administration of the phosphoserine Raf-1 peptides in producing a reversion of oncogenically transformed cells.

Because Raf-1 is activated by Ras and is required for transformation by Ras, the inventors herein believe that inhibition of Raf-1 function will block the transforming effects mediated by a Ras protein. It is generally believed that intracellular Ras protein plays a major role in human carcinogenesis both as an oncogenic protein protein from a mutated ras gene and as a normal Ras protein mediating the effects of a growth-factor oncogene (Prendergast et al. supra). Using standard microinjection techniques, phosphoserine Raf-259 and Raf-621 peptides are injected into the cytoplasm of cells of oncogenically transformed in a manner mediated by a Ras protein and reversion is assessed by detecting changes in the morphology of the transformed cells and by performing cell cycle analysis according to methods well known in the art (Dobrowolski et al, *Mol Cell Biol* 14:5441–5449, 1994; Smith et al., *Nature* 320:540–543, 1986; Kung et al, *Exp Cell Res* 162:363–371, 1986 which are incorporated by reference). Briefly, these experiments are conducted as follows:

NIH 3T3 are transformed by incubating the cells with an oncogene such as the membrane-associaed receptor-like proteins, src, fms and fes (Smith et al, supra). Alternatively, NIH 3T3 cells can be transformed by microinjection of an oncogenic Ras protein such as, for example, p21 Ras proteins (Kung et al, supra).

Transformed cells can be identified morphologically in that they take on a spindle-shaped appearance and in phase-contrast optics the cells become darkened and surrounded by a bright refractile border. In addition, the $^3$H-thymidine incorporation of the transformed cells can be determined by standard methods.

The transformed cells prepared by one of the methods indicated above, are microinjected with a phosphoserine Raf-259 or Raf-621 peptide such as, for example, SEQ ID NO: 10 or SEQ ID NO: 5. Reversion of the cell can then be detected by monitoring cell morphology or $^3$H-thymidine incorporation. Alternatively, the peptide can be microinjected prior to transformation and the prevention of transformation monitored. As a positive control for reversion or prevention of transformation, the c-ras protein the monoclonal antibody, Y13-259, can be microinjected into the cells.

These experiments illustrate the effectiveness of the phosphoserine Raf peptides of the present invention in treating cancer cells.

In view of the above, it will be seen that the several advantages of the invention are achieved and other advantageous results attained.

As various changes could be made in the above methods and compositions without departing from the scope of the invention, it is intended that all matter contained in the above description and shown in the accompanying drawings shall be interpreted as illustrative and not in a limiting sense.

What is claimed is:

1. A method for identifying a pharmacologic agent that inhibits the activation of a signaling protein of the type that binds to a 14-3-3 protein, the method comprising:

forming a mixture comprising a construct containing a 14-3-3 protein or derivative thereof which binds to full-length Raf-1, wherein the protein or derivative is immobilized to a substrate, a labeled peptide of about 6 to about 30 amino acids containing a sequence derived from a Raf-1 sequence surrounding serine-259 or serine-621, where the serine residues in the peptide that correspond to serine-259 and serine-621 are phosphorylated, and said pharmacologic agent;

subjecting the mixture to conditions under which presence of the pharmacologic agent decreases the binding of the labeled peptide to the construct; and detecting the binding of the labeled peptide to the construct wherein a decrease in binding of the labeled peptide indicates a binding of the pharmacologic agent to the construct.

2. The method of claim 1 wherein the peptide contains a sequence as set forth in a member selected from the group consisting of SEQ ID NO: 1, SEQ ID NO: 2, SEQ ID NO: 3.

3. The method of claim 2 wherein the peptide contains the sequence as set forth in SEQ ID NO: 5 or SEQ ID NO: 10.

4. The method of claim 3 wherein the signaling protein is Raf-1.

5. The method of claim 1 wherein the labeled peptide is radioactive.

6. The method of claim 1 wherein the label in the labeled peptide comprises an enzyme or a fluorescer.

7. The method of claim 1 wherein the peptide contains a sequence selected from the group consisting of SEQ ID NO: 27, SEQ ID NO: 28, SEQ ID NO: 30, SEQ ID NO: 31, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, and SEQ ID NO: 58.

8. The method of claim 1 wherein the pharmacologic agent is effective in inhibiting growth or differentiation of a cell.

9. The method of claim 1 wherein the pharmacologic agent is effective in treating cancer, atherosclerosis, or autoimmune disease.

10. A method for identifying a pharmacologic agent that inhibits the activation of a signaling protein of the type that binds to a 14-3-3 protein, the method comprising:

forming a mixture comprising a construct containing a peptide of about 6 to about 30 amino acids containing a sequence derived from a Raf-1 sequence surrounding serine-259 or serine-621 immobilized to a substrate, where the serine residues in the peptide that correspond to serine-259 and serine-621 are phosphorylated, a labeled 14-3-3 protein or derivative thereof which binds to full-length Raf-1, and said pharmacologic agent;

subjecting the mixture to conditions under which presence of the pharmacologic agent decreases the binding of the construct to the labeled 14-3-3 protein or derivative thereof; and detecting the binding of the construct to the labeled 14-3-3 protein or derivative thereof wherein a decrease in binding of the labeled 14-3-3 protein or derivative thereof indicates a binding of the pharmacologic agent to the 14-3-3 protein or derivative thereof.

11. The method of claim 10 wherein the peptide contains a sequence as set forth in a member selected from the group consisting of SEQ ID NO: 1, SEQ ID NO: 2, SEQ ID NO: 3.

12. The method of claim 11 wherein the peptide contains the sequence as set forth in SEQ ID NO:5 or SEQ ID NO: 10.

13. The method of claim 12 wherein the signaling protein is Raf-1.

14. The method of claim 10 wherein the labeled 14-3-3 protein or derivative thereof is radioactive.

15. The method of claim 10 wherein the label in the labeled 14-3-3 protein or derivative thereof comprises an enzyme or a fluorescer.

16. The method of claim 10 wherein the peptide contains a sequence selected from the group consisting of SEQ ID NO: 27, SEQ ID NO: 28, SEQ ID NO: 30, SEQ ID NO: 31, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, and SEQ ID NO: 58.

17. The method of claim 10 wherein the pharmacologic agent is effective in inhibiting growth or differentiation of a cell.

18. The method of claim 10 wherein the pharmacologic agent is effective in treating cancer, atherosclerosis, or autoimmune disease.

19. A method for identifying a pharmacologic agent that inhibits the activation of a signaling protein, the method comprising:

forming a mixture comprising a 14-3-3 protein or derivative thereof which binds to full-length Raf-1, a peptide containing a sequence derived from a Raf-1 sequence surrounding a phosphorylated serine-259 or a phosphorylated serine-621, and said pharmacologic agent, where either the 14-3-3 protein or derivative thereof or the peptide is immobilized to a substrate to form a construct, and where the non-immobilized entity is labeled;

subjecting the mixture to conditions under which presence of the pharmacologic agent decreases the binding of the labeled entity to the construct; and detecting the binding of the labeled entity to the construct wherein a decrease in binding of the labeled entity indicates a binding of the pharmacologic agent to the 14-3-3 protein or derivative thereof.

20. The method of claim 19 wherein the peptide contains a sequence as set forth in a member selected from the group consisting of SEQ ID NO: 1, SEQ ID NO: 2, SEQ ID NO: 3 and derivatives thereof.

21. The method of claim 20 wherein the peptide contains the sequence as set forth in SEQ ID NO: 5 or SEQ ID NO: 10.

22. The method of claim 21 wherein the signaling protein is Raf-1.

23. The method of claim 19 wherein the labeled entity is radioactive.

24. The method of claim 19 wherein the label in the labeled entity comprises an enzyme or a fluorescer.

25. The method of claim 19 wherein the peptide contains a sequence selected from the group consisting of SEQ ID NO: 27, SEQ ID NO: 28, SEQ ID NO: 30, SEQ ID NO: 31, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, and SEQ ID NO: 58.

26. The method of claim 19 wherein the pharmacologic agent is effective in inhibiting growth or differentiation of a cell.

27. The method of claim 19 wherein the pharmacologic agent is effective in treating cancer, atherosclerosis, or autoimmune disease.

* * * * *

```
                         SEQUENCE LISTING (1) GENERAL INFORMATION:

(iii) NUMBER OF SEQUENCES: 58

(2) INFORMATION FOR SEQ ID NO:1:

(i) SEQUENCE CHARACTERISTICS:
             (A) LENGTH: 6 amino acids
             (B) TYPE: amino acid
             (C) STRANDEDNESS:
             (D) TOPOLOGY: linear (ii) MOLECULE TYPE: peptide (ix) FEATURE:
             (A) NAME/KEY: Modified-site
             (B) LOCATION: 3
             (D) OTHER INFORMATION: /note= "Any amino acid"

(ix) FEATURE:
             (A) NAME/KEY: Modified-site
             (B) LOCATION: 4
             (D) OTHER INFORMATION: /note= "A phosphorylated serine"

(ix) FEATURE:
             (A) NAME/KEY: Modified-site
             (B) LOCATION: 5
             (D) OTHER INFORMATION: /note= "Any amino acid"

(xi) SEQUENCE DESCRIPTION: SEQ ID NO:1:

Arg Ser Xaa Xaa Xaa Pro
    1               5

(2) INFORMATION FOR SEQ ID NO:2:

(i) SEQUENCE CHARACTERISTICS:
             (A) LENGTH: 8 amino acids
             (B) TYPE: amino acid
             (C) STRANDEDNESS:
             (D) TOPOLOGY: linear (ii) MOLECULE TYPE: peptide (ix) FEATURE:
             (A) NAME/KEY: Modified-site
             (B) LOCATION: 2
             (D) OTHER INFORMATION: /note= "Any amino acid"

(ix) FEATURE:
             (A) NAME/KEY: Modified-site
```

```
            (B) LOCATION: 5
            (D) OTHER INFORMATION: /note= "Any amino acid"

(ix) FEATURE:
            (A) NAME/KEY: Modified-site
            (B) LOCATION: 6
            (D) OTHER INFORMATION: /note= "A phosphorylated serine"

(ix) FEATURE:
            (A) NAME/KEY: Modified-site
            (B) LOCATION: 7
            (D) OTHER INFORMATION: /note= "Any amino acid"

(xi) SEQUENCE DESCRIPTION: SEQ ID NO:2:

Arg Xaa Arg Ser Xaa Xaa Xaa Pro
1               5

(2) INFORMATION FOR SEQ ID NO:3:

(i) SEQUENCE CHARACTERISTICS:
            (A) LENGTH: 9 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 2
            (D) OTHER INFORMATION: /note= "Any amino acid"

(ix) FEATURE:
            (A) NAME/KEY: Modified-site
            (B) LOCATION: 3
            (D) OTHER INFORMATION: /note= "Any amino acid"

(ix) FEATURE:
            (A) NAME/KEY: Modified-site
            (B) LOCATION: 6
            (D) OTHER INFORMATION: /note= "Any amino acid"

(ix) FEATURE:
            (A) NAME/KEY: Modified-site
            (B) LOCATION: 7
            (D) OTHER INFORMATION: /note= "A phosphorylated serine"

(ix) FEATURE:
            (A) NAME/KEY: Modified-site
            (B) LOCATION: 8
            (D) OTHER INFORMATION: /note= "Any amino acid"

(xi) SEQUENCE DESCRIPTION: SEQ ID NO:3:

Lys Xaa Xaa Arg Ser Xaa Xaa Xaa Pro
1               5

(2) INFORMATION FOR SEQ ID NO:4:

(i) SEQUENCE CHARACTERISTICS:
            (A) LENGTH: 15 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:4:

Leu Ser Gln Arg Gln Arg Ser Thr Ser Thr Pro Asn Val His Met
    1               5                   10                  15

(2) INFORMATION FOR SEQ ID NO:5:

(i) SEQUENCE CHARACTERISTICS:
```

(A) LENGTH: 15 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 9
            (D) OTHER INFORMATION: /note= "A phosphorylated serine"

(xi) SEQUENCE DESCRIPTION: SEQ ID NO:5:

Leu Ser Gln Arg Gln Arg Ser Thr Xaa Thr Pro Asn Val His Ala
1               5                   10                  15

(2) INFORMATION FOR SEQ ID NO:6:

(i) SEQUENCE CHARACTERISTICS:
            (A) LENGTH: 10 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 7
            (D) OTHER INFORMATION: /note= "A phosphorylated threonine"

(xi) SEQUENCE DESCRIPTION: SEQ ID NO:6:

Arg Arg Arg Glu Glu Glu Xaa Glu Glu Glu
1               5                   10

(2) INFORMATION FOR SEQ ID NO:7:

(i) SEQUENCE CHARACTERISTICS:
            (A) LENGTH: 8 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /note= "A phosphorylated tyrosine"

(xi) SEQUENCE DESCRIPTION: SEQ ID NO:7:

Xaa Glu Glu Ile Ser Pro Ala Lys
1               5

(2) INFORMATION FOR SEQ ID NO:8:

(i) SEQUENCE CHARACTERISTICS:
            (A) LENGTH: 6 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:8:

Arg Ser Thr Ser Thr Pro
1               5

(2) INFORMATION FOR SEQ ID NO:9:

(i) SEQUENCE CHARACTERISTICS:

```
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:9:

Arg Ser Ala Ser Glu Pro
1               5

(2) INFORMATION FOR SEQ ID NO:10:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 9
        (D) OTHER INFORMATION: /note= "A phosphorylated serine"

(xi) SEQUENCE DESCRIPTION: SEQ ID NO:10:

Leu Pro Lys Ile Asn Arg Ser Ala Xaa Glu Pro Ser Leu His Arg
1               5                   10                  15

(2) INFORMATION FOR SEQ ID NO:11:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

GAGGATCCAC AATGGATAAA AGTGAG                                  26

(2) INFORMATION FOR SEQ ID NO:12:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

GAGAATTCTT AGTTCTCTCC CTCCCCA                                 27

(2) INFORMATION FOR SEQ ID NO:13:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

GAGGATCCGG GGACCGGGAG CAGCTG                                  26
```

(2) INFORMATION FOR SEQ ID NO:14:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

GAGAATTCTC AGTTGCCTTC TCCTGC                                      26

(2) INFORMATION FOR SEQ ID NO:15:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

GAGGATCCGA GAAGACTGAG CTGATC                                      26

(2) INFORMATION FOR SEQ ID NO:16:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

GAGAATTCTT AGTTTTCAGC CCCTTC                                      26

(2) INFORMATION FOR SEQ ID NO:17:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

ATTGGATCCG ATAAAAATGA GCTGGTTC                                  28

(2) INFORMATION FOR SEQ ID NO:18:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

TTGAATTCAA TTTTCCCCTC CTTCTCCT                                  28

(2) INFORMATION FOR SEQ ID NO:19:

(i) SEQUENCE CHARACTERISTICS:
        (A) LENGTH: 10 amino acids (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 7
            (D) OTHER INFORMATION: /note= "A phosphorylated threonine"

(xi) SEQUENCE DESCRIPTION: SEQ ID NO:19:

Arg Arg Arg Glu Glu Glu Xaa Glu Glu Glu
1               5                   10

(2) INFORMATION FOR SEQ ID NO:20:

(i) SEQUENCE CHARACTERISTICS:
            (A) LENGTH: 8 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /note= "A phosphorylated tyrosine"

(xi) SEQUENCE DESCRIPTION: SEQ ID NO:20:

Xaa Glu Glu Ile Gln Pro Ala Lys
1               5

(2) INFORMATION FOR SEQ ID NO:21:

(i) SEQUENCE CHARACTERISTICS:
            (A) LENGTH: 15 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 7
            (D) OTHER INFORMATION: /note= "A phosphorylated serine"

(xi) SEQUENCE DESCRIPTION: SEQ ID NO:21:

Leu Ser Gln Arg Gln Arg Xaa Thr Ser Thr Pro Asn Val His Ala
1               5                   10                  15

(2) INFORMATION FOR SEQ ID NO:22:

(i) SEQUENCE CHARACTERISTICS:
            (A) LENGTH: 15 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 7
            (D) OTHER INFORMATION: /note= "A phosphorylated serine"

(ix) FEATURE:
            (A) NAME/KEY: Modified-site
            (B) LOCATION: 9
            (D) OTHER INFORMATION: /note= "A phosphorylated serine"

```
    (xi) SEQUENCE DESCRIPTION: SEQ ID NO:22:

Leu Ser Gln Arg Gln Arg Xaa Thr Xaa Thr Pro Asn Val His Ala
1               5                  10                  15

(2) INFORMATION FOR SEQ ID NO:23:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /note= "Any amino acid"

(ix) FEATURE:
        (A) NAME/KEY: Modified-site
        (B) LOCATION: 5
        (D) OTHER INFORMATION: /note= "Any amino acid"

(ix) FEATURE:
        (A) NAME/KEY: Modified-site
        (B) LOCATION: 7
        (D) OTHER INFORMATION: /note= "Any amino acid"

(xi) SEQUENCE DESCRIPTION: SEQ ID NO:23:

Arg Xaa Arg Ser Xaa Ser Xaa Pro
1               5

(2) INFORMATION FOR SEQ ID NO:24:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /note= "Any amino acid"

(ix) FEATURE:
        (A) NAME/KEY: Modified-site
        (B) LOCATION: 5
        (D) OTHER INFORMATION: /note= "Any amino acid"

(xi) SEQUENCE DESCRIPTION: SEQ ID NO:24:

Arg Ser Xaa Ser Xaa Pro
1               5

(2) INFORMATION FOR SEQ ID NO:25:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /note= "Any amino acid"

(ix) FEATURE:
```

```
            (A) NAME/KEY: Modified-site
            (B) LOCATION: 5
            (D) OTHER INFORMATION: /note= "Any amino acid"

(ix) FEATURE:
            (A) NAME/KEY: Modified-site
            (B) LOCATION: 6
            (D) OTHER INFORMATION: /note= "A phosphorylated serine"

(ix) FEATURE:
            (A) NAME/KEY: Modified-site
            (B) LOCATION: 7
            (D) OTHER INFORMATION: /note= "Any amino acid"

(xi) SEQUENCE DESCRIPTION: SEQ ID NO:25:

Arg Xaa Arg Ser Xaa Xaa Xaa Pro
1               5

(2) INFORMATION FOR SEQ ID NO:26:

(i) SEQUENCE CHARACTERISTICS:
            (A) LENGTH: 15 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 9
            (D) OTHER INFORMATION: /note= "A phosphorylated serine"

(xi) SEQUENCE DESCRIPTION: SEQ ID NO:26:

Leu Ser Gln Ala Gln Ala Ser Thr Xaa Thr Pro Asn Val His Ala
1               5                  10                  15

(2) INFORMATION FOR SEQ ID NO:27:

(i) SEQUENCE CHARACTERISTICS:
            (A) LENGTH: 15 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 9
            (D) OTHER INFORMATION: /note= "A phosphorylated serine"

(xi) SEQUENCE DESCRIPTION: SEQ ID NO:27:

Leu Ser Gln Ala Gln Arg Ser Thr Xaa Thr Pro Asn Val His Ala
1               5                  10                  15

(2) INFORMATION FOR SEQ ID NO:28:

(i) SEQUENCE CHARACTERISTICS:
            (A) LENGTH: 15 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 9
            (D) OTHER INFORMATION: /note= "A phosphorylated serine"

(xi) SEQUENCE DESCRIPTION: SEQ ID NO:28:
```

Leu Ser Gln Arg Gln Ala Ser Thr Xaa Thr Pro Asn Val His Ala
1               5                   10                  15

(2) INFORMATION FOR SEQ ID NO:29:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 9
        (D) OTHER INFORMATION: /note= "A phosphorylated serine"

(xi) SEQUENCE DESCRIPTION: SEQ ID NO:29:

Leu Ser Gln Ala Gln Ser Arg Thr Xaa Thr Pro Asn Val His Ala
1               5                   10                  15

(2) INFORMATION FOR SEQ ID NO:30:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 9
        (D) OTHER INFORMATION: /note= "A phosphorylated serine"

(xi) SEQUENCE DESCRIPTION: SEQ ID NO:30:

Leu Ser Gln Ala Arg Gln Ser Thr Xaa Thr Pro Asn Val His Ala
1               5                   10                  15

(2) INFORMATION FOR SEQ ID NO:31:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 9
        (D) OTHER INFORMATION: /note= "A phosphorylated serine"

(xi) SEQUENCE DESCRIPTION: SEQ ID NO:31:

Leu Ser Gln Arg Gln Arg Ser Thr Xaa Thr Ala Asn Val His Met
1               5                   10                  15

(2) INFORMATION FOR SEQ ID NO:32:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site (B) LOCATION: 3
            (D) OTHER INFORMATION: /note= "Any amino acid"

(ix) FEATURE:
            (A) NAME/KEY: Modified-site
            (B) LOCATION: 5
            (D) OTHER INFORMATION: /note= "Any amino acid"

(xi) SEQUENCE DESCRIPTION: SEQ ID NO:32:

Arg Ser Xaa Ser Xaa Pro
1               5

(2) INFORMATION FOR SEQ ID NO:33:

(i) SEQUENCE CHARACTERISTICS:
            (A) LENGTH: 15 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 4
            (D) OTHER INFORMATION: /note= "Any amino acid"

(ix) FEATURE:
            (A) NAME/KEY: Modified-site
            (B) LOCATION: 9
            (D) OTHER INFORMATION: /note= "A phosphorylated serine"

(xi) SEQUENCE DESCRIPTION: SEQ ID NO:33:

Leu Pro Lys Xaa Asn Arg Ser Ala Xaa Glu Pro Ser Leu His Arg
1               5                   10                  15

(2) INFORMATION FOR SEQ ID NO:34:

(i) SEQUENCE CHARACTERISTICS:
            (A) LENGTH: 15 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 6
            (D) OTHER INFORMATION: /note= "Any amino acid"

(ix) FEATURE:
            (A) NAME/KEY: Modified-site
            (B) LOCATION: 9
            (D) OTHER INFORMATION: /note= "A phosphorylated serine"

(xi) SEQUENCE DESCRIPTION: SEQ ID NO:34:

Leu Pro Lys Ile Asn Xaa Ser Ala Xaa Glu Pro Ser Leu His Arg
1               5                   10                  15

(2) INFORMATION FOR SEQ ID NO:35:

(i) SEQUENCE CHARACTERISTICS:
            (A) LENGTH: 16 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 8

(D) OTHER INFORMATION: /note= "Any amino acid"

(ix) FEATURE:
            (A) NAME/KEY: Modified-site
            (B) LOCATION: 10
            (D) OTHER INFORMATION: /note= "A phosphorylated serine"

(xi) SEQUENCE DESCRIPTION: SEQ ID NO:35:

Leu Pro Lys Ile Asn Arg Ser Xaa Ala Xaa Glu Pro Ser Leu His Arg
1               5                   10                  15

(2) INFORMATION FOR SEQ ID NO:36:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 8
        (D) OTHER INFORMATION: /note= "Any amino acid"

(ix) FEATURE:
        (A) NAME/KEY: Modified-site
        (B) LOCATION: 9
        (D) OTHER INFORMATION: /note= "A phosphorylated serine"

(xi) SEQUENCE DESCRIPTION: SEQ ID NO:36:

Leu Pro Lys Ile Asn Arg Ser Xaa Xaa Glu Pro Ser Leu His Arg
1               5                   10                  15

(2) INFORMATION FOR SEQ ID NO:37:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 9
        (D) OTHER INFORMATION: /note= "A phosphorylated serine"

(ix) FEATURE:
        (A) NAME/KEY: Modified-site
        (B) LOCATION: 10
        (D) OTHER INFORMATION: /note= "Any amino acid"

(xi) SEQUENCE DESCRIPTION: SEQ ID NO:37:

Leu Pro Lys Ile Asn Arg Ser Ala Xaa Xaa Pro Ser Leu His Arg
1               5                   10                  15

(2) INFORMATION FOR SEQ ID NO:38:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 9
        (D) OTHER INFORMATION: /note= "A phosphorylated serine"

(ix) FEATURE:
            (A) NAME/KEY: Modified-site
            (B) LOCATION: 11
            (D) OTHER INFORMATION: /note= "Any amino acid"

(xi) SEQUENCE DESCRIPTION: SEQ ID NO:38:

Leu Pro Lys Ile Asn Arg Ser Ala Xaa Glu Xaa Ser Leu His Arg
                  5                  10                  15

(2) INFORMATION FOR SEQ ID NO:39:

(i) SEQUENCE CHARACTERISTICS:
          (A) LENGTH: 6 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:39:

Arg Ser Thr Ser Thr Pro
1               5

(2) INFORMATION FOR SEQ ID NO:40:

(i) SEQUENCE CHARACTERISTICS:
          (A) LENGTH: 6 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:40:

Arg Ser Ala Ser Glu Pro
1               5

(2) INFORMATION FOR SEQ ID NO:41:

(i) SEQUENCE CHARACTERISTICS:
          (A) LENGTH: 6 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:41:

Arg Ser Ser Ser Ala Pro
1               5

(2) INFORMATION FOR SEQ ID NO:42:

(i) SEQUENCE CHARACTERISTICS:
          (A) LENGTH: 6 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:42:

Arg Ser His Ser Tyr Pro
1               5

(2) INFORMATION FOR SEQ ID NO:43:

(i) SEQUENCE CHARACTERISTICS:

(A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:43:

Arg Ser Pro Ser Met Pro
1               5

(2) INFORMATION FOR SEQ ID NO:44:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:44:

Arg Ser Lys Ser Ala Pro
1               5

(2) INFORMATION FOR SEQ ID NO:45:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:45:

Arg Ser Pro Ser Ser Pro
1               5

(2) INFORMATION FOR SEQ ID NO:46:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:46:

Arg Ser Gln Ser Gln Asn
1               5

(2) INFORMATION FOR SEQ ID NO:47:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:47:

Arg His Ala Ser Ser Pro
1               5

(2) INFORMATION FOR SEQ ID NO:48:

```
    (i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 4
        (D) OTHER INFORMATION: /note= "A phosphorylated serine"

(xi) SEQUENCE DESCRIPTION: SEQ ID NO:48:

Arg Ser Arg Xaa Ala Pro
1               5

(2) INFORMATION FOR SEQ ID NO:49:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 4
        (D) OTHER INFORMATION: /note= "A phosphorylated serine"

(xi) SEQUENCE DESCRIPTION: SEQ ID NO:49:

Arg Ser Cys Xaa Ile Pro
1               5

(2) INFORMATION FOR SEQ ID NO:50:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 4
        (D) OTHER INFORMATION: /note= "A phosphorylated serine"

(xi) SEQUENCE DESCRIPTION: SEQ ID NO:50:

Arg Ser Thr Xaa Arg Pro
1               5

(2) INFORMATION FOR SEQ ID NO:51:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 4
        (D) OTHER INFORMATION: /note= "A phosphorylated serine"

(xi) SEQUENCE DESCRIPTION: SEQ ID NO:51:

Arg Ser Pro Xaa Phe Pro
```

(2) INFORMATION FOR SEQ ID NO:52:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 4
        (D) OTHER INFORMATION: /note= "A phosphorylated serine"

(xi) SEQUENCE DESCRIPTION: SEQ ID NO:52:

Arg Ser Glu Xaa Ser Pro
1               5

(2) INFORMATION FOR SEQ ID NO:53:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 4
        (D) OTHER INFORMATION: /note= "A phosphorylated serine"

(xi) SEQUENCE DESCRIPTION: SEQ ID NO:53:

Arg Ser Pro Xaa Ile Pro
1               5

(2) INFORMATION FOR SEQ ID NO:54:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 4
        (D) OTHER INFORMATION: /note= "A phosphorylated serine"

(xi) SEQUENCE DESCRIPTION: SEQ ID NO:54:

Arg Ser Pro Xaa Lys Pro
1               5

(2) INFORMATION FOR SEQ ID NO:55:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 4

-continued (D) OTHER INFORMATION: /note= "A phosphorylated serine"

(xi) SEQUENCE DESCRIPTION: SEQ ID NO:55:

Arg Ser Pro Xaa Gly Pro
1               5

(2) INFORMATION FOR SEQ ID NO:56:

(i) SEQUENCE CHARACTERISTICS:
            (A) LENGTH: 6 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 4
            (D) OTHER INFORMATION: /note= "A phosphorylated serine"

(xi) SEQUENCE DESCRIPTION: SEQ ID NO:56:

Arg Ser Val Xaa Ser Pro
1               5

(2) INFORMATION FOR SEQ ID NO:57:

(i) SEQUENCE CHARACTERISTICS:
            (A) LENGTH: 6 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 4
            (D) OTHER INFORMATION: /note= "A phosphorylated serine"

(xi) SEQUENCE DESCRIPTION: SEQ ID NO:57:

Arg Ser Arg Xaa Tyr Pro
1               5

(2) INFORMATION FOR SEQ ID NO:58:

(i) SEQUENCE CHARACTERISTICS:
            (A) LENGTH: 6 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 4
            (D) OTHER INFORMATION: /note= "A phosphorylated serine"

(xi) SEQUENCE DESCRIPTION: SEQ ID NO:58:

Arg Ser Gln Xaa Lys Pro
1               5